US012729177B2

(12) United States Patent
Cohen et al.

(10) Patent No.: US 12,729,177 B2
(45) Date of Patent: Sep. 8, 2026

(54) SMALL MOLECULES PROMOTING SYMPATHETIC NERVE REGENERATION

(71) Applicant: OREGON HEALTH & SCIENCE UNIVERSITY, Portland, OR (US)

(72) Inventors: Michael Cohen, Portland, OR (US); Beth Habecker, Portland, OR (US); Haihong Jin, Portland, OR (US); Ryan Gardner, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 619 days.

(21) Appl. No.: 18/044,052

(22) PCT Filed: Aug. 30, 2021

(86) PCT No.: PCT/US2021/048283
§ 371 (c)(1),
(2) Date: Mar. 3, 2023

(87) PCT Pub. No.: WO2022/051233
PCT Pub. Date: Mar. 10, 2022

(65) Prior Publication Data

US 2023/0373907 A1 Nov. 23, 2023

Related U.S. Application Data

(60) Provisional application No. 63/074,702, filed on Sep. 4, 2020.

(51) Int. Cl.
*C07C 233/00* (2006.01)
*C07C 205/59* (2006.01)
*C07C 229/56* (2006.01)
*C07C 233/55* (2006.01)

(52) U.S. Cl.
CPC .......... *C07C 233/55* (2013.01); *C07C 205/59* (2013.01); *C07C 229/56* (2013.01); *C07C 2601/16* (2017.05)

(58) Field of Classification Search
CPC ... C07C 233/00; C07C 233/55; C07C 229/56; C07C 205/59; C07C 2601/16; C07C 2601/14
See application file for complete search history.

(56) References Cited

FOREIGN PATENT DOCUMENTS

| | | | |
|---|---|---|---|
| WO | WO-2008069611 A1 * | 6/2008 | C07D 263/10 |
| WO | WO-2021113062 A1 * | 6/2021 | A61K 31/196 |

* cited by examiner

*Primary Examiner* — Kamal A Saeed
*Assistant Examiner* — Sagar Patel

(57) ABSTRACT

The present invention concerns novel compounds, pharmaceutical compositions, and methods for promoting nerve regeneration, particularly including sympathetic nerve regeneration in the heart following a myocardial infarction and damage to the central nervous system, such as after a cerebrovascular accident, through inhibitory extracellular matrix that includes chondroitin sulfate roteoglycans (CSPG).

20 Claims, 9 Drawing Sheets

FIG. 6B
Veh
FIG. 6C
MI + HJ2
FIG. 6D
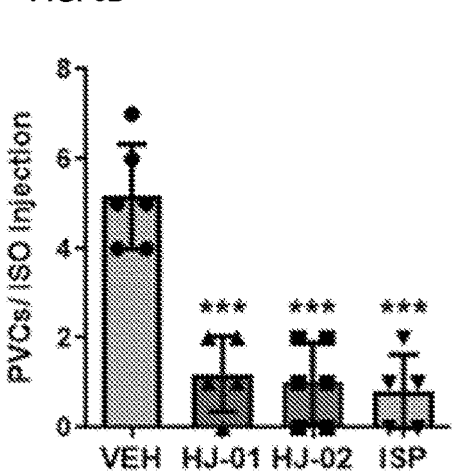
FIG. 7A
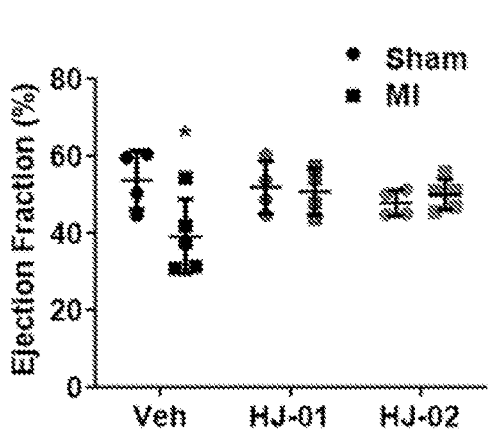
FIG. 7B
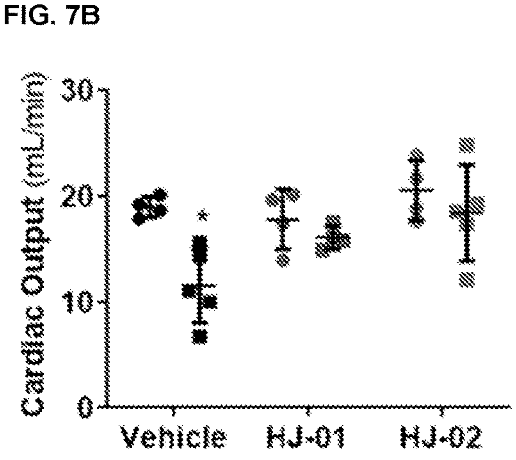
FIG. 7C
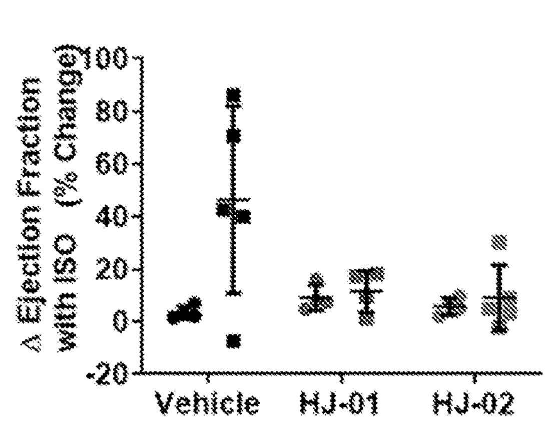

6
4
2
0.0
% Cells aSMA +
Vehicle
ISP
HJ2

SMALL MOLECULES PROMOTING SYMPATHETIC NERVE REGENERATION

STATEMENT OF GOVERNMENT RIGHTS

This invention was made with government support under HL093056 awarded by the National Institutes of Health. The government has certain rights in the invention.

FIELD OF THE INVENTION

The present invention concerns novel compounds, pharmaceutical compositions, and methods for promoting nerve regeneration, particularly including sympathetic nerve regeneration in the heart following a myocardial infarction, through inhibitory extracellular matrix that includes chondroitin sulfate proteoglycans (CSPG).

BACKGROUND OF THE INVENTION

Each year over 7 million people suffer a myocardial infarction (MI), which damages cardiac sympathetic nerves in addition to leaving a scar in the heart. Cardiac sympathetic denervation after MI predicts arrhythmia susceptibility in clinical studies. Chondroitin sulfate proteoglycans (CSPGs) in the cardiac scar prevent nerve regeneration by interacting with neuronal protein tyrosine phosphatase receptor sigma (PTPσ.). CSPGs also prevent nerve regrowth after traumatic brain injury and spinal cord injury, and there are no small molecule therapeutics to promote nerve regeneration through CSPG-containing scars. Here we describe the development of compounds (HJ-01, HJ-02) that promote sympathetic nerve regeneration in vitro and in vivo by disrupting PTPσ interactions with tropomyosin receptor kinases (Trks). Restoring innervation prevented arrhythmias, consistent with earlier studies of cardiac reinnervation. Surprisingly, HJ-01 and HJ-02 also decreased infarct size and prevented the loss of cardiac output, despite treatment beginning three days after MI. Other approaches to restore innervation had no effect on infarct size, suggesting the cardiac protection was a selective effect of HJ-01 and HJ-02. Our compounds had multiple beneficial effects in the heart after MI, and they may prove useful in other contexts where CSPGs prevent nerve regeneration.

Coronary heart disease is a leading cause of death in the world, with more than 7.2 million people suffering a myocardial infarction (MI) each year[1]. MI damages cardiac myocytes, impairing cardiac function and often leading to heart failure[2]. Myocardial infarction also disrupts cardiac sympathetic nerves[3-7], which normally release norepinephrine (NE) to increase heart rate, contractility, and relaxation by activating β adrenergic receptors (β-AR) on cardiac myocytes. Several clinical trials have concluded that the amount of sympathetic denervation in the heart after MI predicts the probability of serious ventricular arrhythmias[8-10].

The lack of sympathetic nerve regeneration after MI is due to chondroitin sulfate proteoglycans (CSPGs) in the cardiac scar interacting with protein tyrosine phosphatase receptor sigma (PTPσ) on the neurons[11]. We previously showed that targeting PTPσ genetically[11] or with the peptide ISP (Intracellular Sigma Peptide;[12]) restored sympathetic innervation to the scar and borderzone[13]. Sympathetic reinnervation restored NE content and normalized myocyte β-AR signaling, cardiac electrophysiology, and myocyte $Ca^{2+}$ handling, rendering hearts resistant to isoproterenol-induced arrhythmias[13].

The mechanisms by which PTPσ inhibits sympathetic axon outgrowth are not fully understood, but interactions with neurotrophin receptors from the Trk receptor family (TrkA, TrkB, and TrkC) are thought to play a key role[14,15]. PTPσ binds to and dephosphorylates Trk receptors, thus inhibiting their kinase activity[15]. In sympathetic nerves Nerve Growth Factor (NGF) activation of TrkA stimulates axon extension, while dephosphorylation of TrkA suppresses axon growth. Thus, disrupting the interaction between TrkA and PTPσ should enhance axon outgrowth over CSPGs.

Here, we describe natural product-inspired small molecules (HJ-01 and HJ-02) that do not inhibit PTPσ activity, but instead disrupt the interaction between PTPσ and TrkA. HJ-01 and HJ-02 restored sympathetic axon outgrowth across CSPGs in vitro, enhanced Trk signaling, and promoted nerve regeneration into the cardiac scar after myocardial infarction.

SUMMARY OF THE INVENTION

Provided is a compound of Formula (I):

(I)

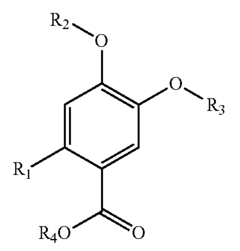

wherein:

$R_1$ is a moiety selected from the group of:

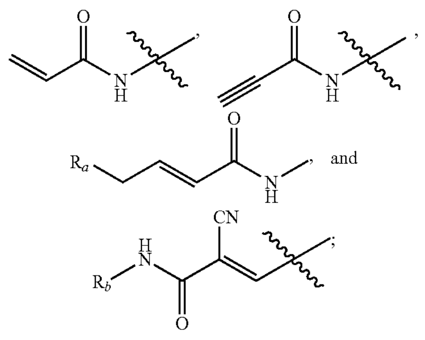

, , , and ;

$R_a$ is selected from the group of $C_1$-$C_6$ straight or branched alkyl, $C_2$-$C_6$ straight or branched alkenyl, $C_2$-$C_6$ straight or branched alkynyl, $C_3$-$C_6$ cycloalkyl, and $—(CH_2)_{n1}$-$C_3$-$C_6$ cycloalkyl;

$R_b$ is selected from the group of $C_1$-$C_6$ straight or branched alkyl, $C_2$-$C_6$ straight or branched alkenyl, $C_2$-$C_6$ straight or branched alkynyl, $C_3$-$C_6$ cycloalkyl, and $—(CH_2)_{n2}$-$C_3$-$C_6$ cycloalkyl;

n1 in each instance is an integer independently selected from the group of 1, 2, 3, 4, 5, and 6;

n2 in each instance is an integer independently selected from the group of 1, 2, 3, 4, 5, and 6;

$R_2$ is selected from the group of $C_1$-$C_4$ straight or branched alkyl, $C_2$-$C_4$ straight or branched alkenyl, and $C_2$-$C_4$ straight or branched alkynyl;

$R_3$ is selected from the group of $C_1$-$C_8$ straight or branched alkyl, $C_2$-$C_6$ straight or branched alkenyl, and straight or branched $C_2$-$C_6$ alkynyl, $C_3$-$C_6$ cycloalkyl, and $-(CH_2)_{n1}$-$C_3$-$C_6$ cycloalkyl; and $R_4$ is selected from the group of H, $C_1$-$C_6$ straight or branched alkyl, $C_2$-$C_6$ straight or branched alkenyl, $C_2$-$C_6$ straight or branched alkynyl, $C_3$-$C_6$ cycloalkyl, $-(CH_2)_{n2}$-$C_3$-$C_6$ cycloalkyl, $C_4$-$C_6$ cycloalkenyl, $-(CH_2)_{n2}$-$C_4$-$C_6$ cycloalkenyl, phenyl, $-(CH_2)_{n2}$-phenyl, 4- to 6-membered heterocyclyl, $-(CH_2)_{n2}$-4- to 6-membered heterocyclyl, heteroaromatic, and $-(CH_2)_{n2}$-heteroaromatic;

with the proviso that, when $R_1$ is:

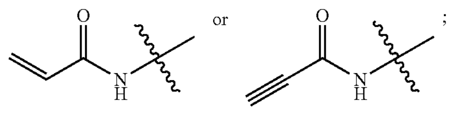

$R_2$ is methyl; and $R_4$ is hydrogen, then $R_3$ is not methyl;

or a pharmaceutically acceptable salt, pharmaceutically acceptable co-crystal, pharmaceutically acceptable ester, pharmaceutically acceptable solvate, hydrate, isomer (including optical isomers, racemates, or other mixtures thereof), tautomer, isotope, polymorph, or a pharmaceutically acceptable prodrug thereof.

DETAILED DESCRIPTION OF THE INVENTION

Figure 1A:
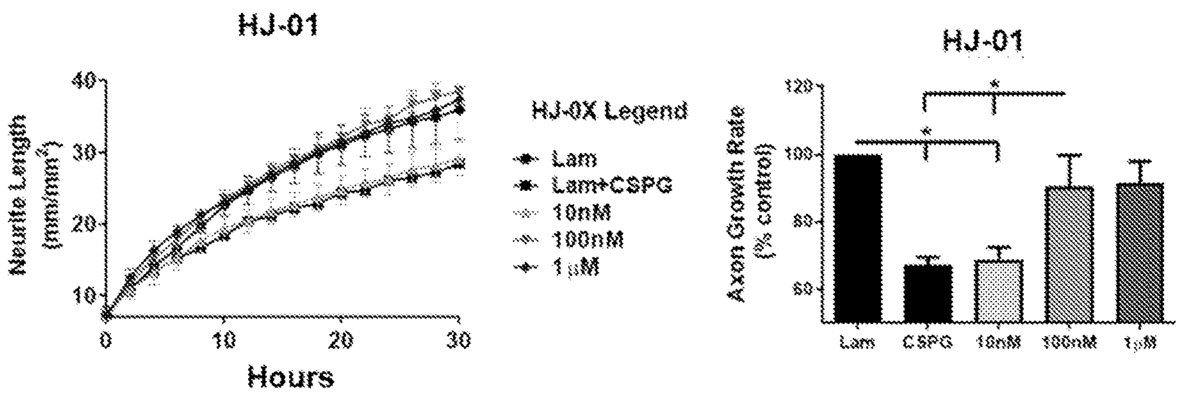
FIG. 1A provides graphs representing quantification of sympathetic axon growth rate on Laminin or CSPGS in the presence of vehicle or HJ-01.
Figure 1B:
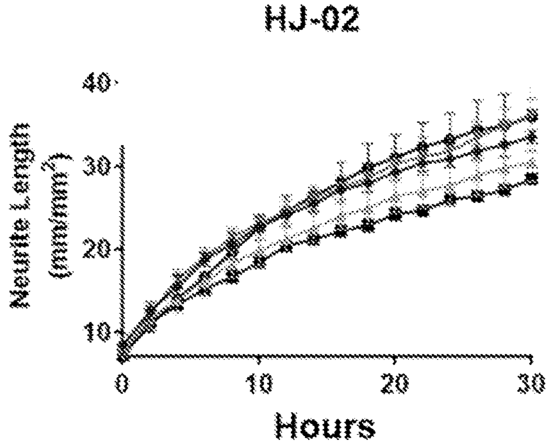
FIG. 1B provides graphs representing quantification of sympathetic axon growth rate on Laminin or CSPGS in the presence of vehicle or HJ-02.
Figure 1B:
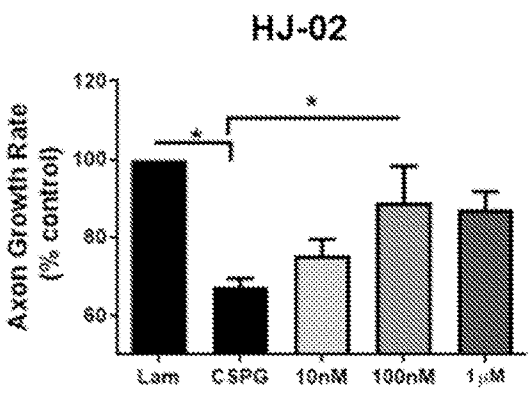
Figure 1C:
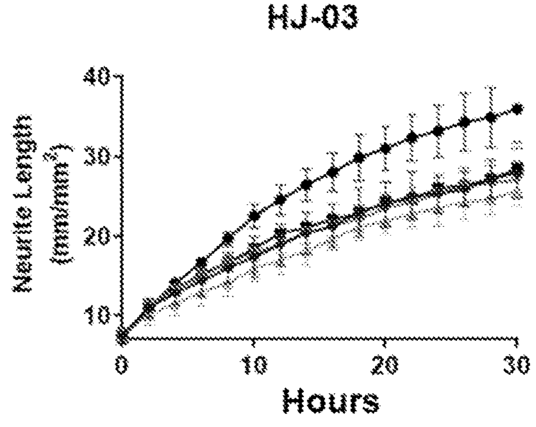
FIG. 1C provides graphs representing quantification of sympathetic axon growth rate on Laminin or CSPGS in the presence of vehicle or HJ-03.
Figure 1C:
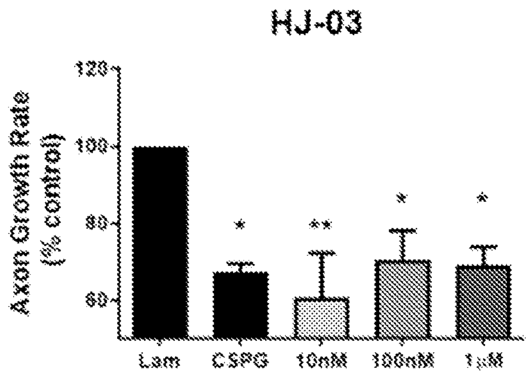
Figure 1D:
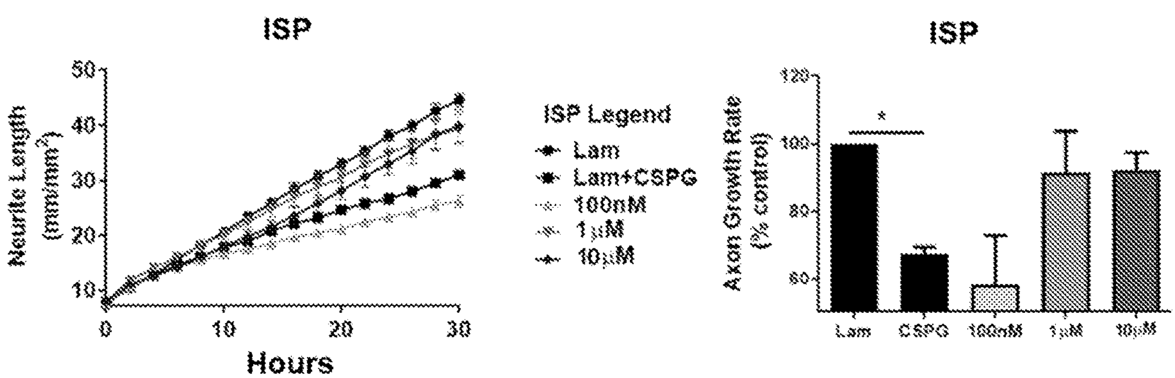
FIG. 1D provides graphs representing quantification of sympathetic axon growth rate on Laminin or CSPGS in the presence of vehicle or ISP.

One embodiment provides a compound of Formula (I), as defined above, wherein $R_3$ is selected from the group of $C_2$-$C_8$ straight or branched alkyl, $C_2$-$C_6$ straight or branched alkenyl, and straight or branched $C_2$-$C_6$ alkynyl, $C_3$-$C_6$ cycloalkyl, and $-(CH_2)_{n1}-C_3$-$C_6$ cycloalkyl; and all other variables, including $R_1$, $R_2$, $R_4$, $R_a$, $R_b$, n1, and n2 are as defined for Formula (I), above; or a pharmaceutically acceptable salt, pharmaceutically acceptable co-crystal, pharmaceutically acceptable ester, pharmaceutically acceptable solvate, hydrate, isomer (including optical isomers, racemates, or other mixtures thereof), tautomer, isotope, polymorph, or a pharmaceutically acceptable prodrug thereof.

One embodiment provides a compound of Formula (I), as defined above, wherein $R_3$ is selected from the group of $C_3$-$C_8$ straight or branched alkyl; and all other variables, including $R_1$, $R_2$, $R_4$, $R_a$, $R_b$, n1, and n2 are as defined for Formula (I), above; or a pharmaceutically acceptable salt, pharmaceutically acceptable co-crystal, pharmaceutically acceptable ester, pharmaceutically acceptable solvate, hydrate, isomer (including optical isomers, racemates, or other mixtures thereof), tautomer, isotope, polymorph, or a pharmaceutically acceptable prodrug thereof.

Three separate embodiments provide, respectively, a compound of Formula (Ia), Formula (Ib), and Formula (Ic):

(Ia)

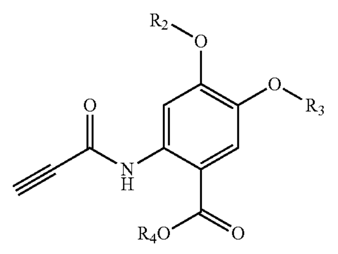

-continued (Ib)

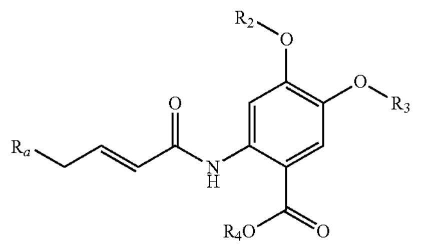

and (Ic)

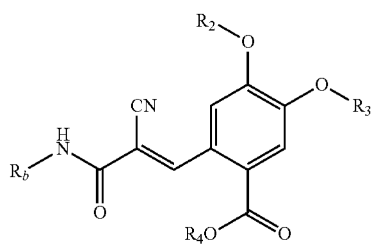

wherein, in each instance where they are present, $R_a$, $R_b$, $R_2$, $R_3$, $R_4$, n1, and n2 are as defined above for Formula (I); or a pharmaceutically acceptable salt, pharmaceutically acceptable co-crystal, pharmaceutically acceptable ester, pharmaceutically acceptable solvate, hydrate, isomer (including optical isomers, racemates, or other mixtures thereof), tautomer, isotope, polymorph, or a pharmaceutically acceptable prodrug thereof.

A further embodiment provides a compound of the Formula (II):

(II)

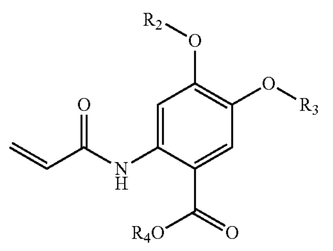

wherein $R_2$, $R_3$, and $R_4$ are as defined above for Formula (I); or a pharmaceutically acceptable salt, pharmaceutically acceptable co-crystal, pharmaceutically acceptable ester, pharmaceutically acceptable solvate, hydrate, isomer (including optical isomers, racemates, or other mixtures thereof), tautomer, isotope, polymorph, or a pharmaceutically acceptable prodrug thereof.

Within each of the embodiments described herein for a compound of Formula (I), Formula (Ia), Formula (Ib), Formula (Ic), and Formula (II), there is a further embodiment wherein all variables are as defined for the embodiment in question, except that $R_2$ is methyl.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is $C_2$-$C_8$ straight or branched alkyl.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is selected from the group of cyclopropyl, cyclobutyl, cyclopentyl, cyclohexyl:

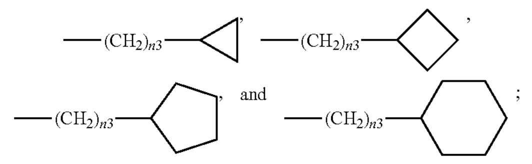

and n3 in each instance is an integer independently selected from the group of 1, 2, 3, 4, 5, and 6.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is a moiety of the formula:

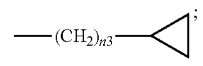

wherein n3 is an integer selected from the group of 1, 2, 3, 4, 5, and 6.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is a moiety of the formula:

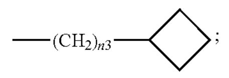

wherein n3 is an integer selected from the group of 1, 2, 3, 4, 5, and 6.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is a moiety of the formula:

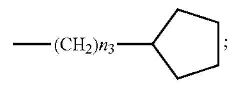

wherein n3 is an integer selected from the group of 1, 2, 3, 4, 5, and 6.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is a moiety of the formula:

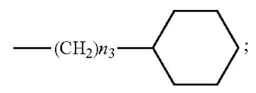

wherein n3 is an integer selected from the group of 1, 2, 3, 4, 5, and 6.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is a moiety of the formula:

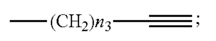

wherein n3 is an integer selected from the group of 1, 2, 3, 4, 5, and 6.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is an alkenyl chain having 2, 3, 4, 5, or 6 carbon atoms and 1 or 2 points of unsaturation (double bonds along the alkenyl chain).

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is an alkenyl chain of the formula: $—(CH_2)n_4\text{-}CH{=}CH_2$; wherein n4 is an integer selected from the group of 1, 2, 3, 4, and 5.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is an alkenyl chain of the formula: $—(CH_2)n_4\text{-}CH{=}CH—(CH_2)n_5\text{-}CH{=}CH_2$; wherein n4 is an integer selected from the group of 1, 2, 3, 4, and 5; n5 is an integer selected from the group of 1, 2, 3, 4, and 5; with the proviso that the sum of n4 and n5 is not greater than 6.

Within each of the embodiments described herein for a compound of Formula (I), Formula (Ia), Formula (Ib), Formula (Ic), and Formula (II), there is a further embodiment wherein all variables are as defined for the embodiment in question, except that $R_3$ is an alkenyl chain of the formula: $—(CH_2)n_4\text{-}CH{=}CH—(CH_2)n_5\text{-}CH{=}CH—R_5$; wherein $R_5$ is $C_1$-$C_6$ straight or branched alkyl; n4 is an integer selected from the group of 1, 2, 3, 4, and 5; n5 is an integer selected from the group of 1, 2, 3, 4, and 5; with the proviso that the sum of n4 and n5 is not greater than 6.

Within each of the embodiments described herein for a compound of Formula (I), Formula (Ia), Formula (Ib), Formula (Ic), and Formula (II), there is a further embodiment wherein all variables are as defined for the embodiment in question, except that $R_4$ is selected from the group of H, $C_1$-$C_6$ alkyl, phenyl, and benzyl.

Within each of the embodiments described herein for a compound of Formula (I), Formula (Ia), Formula (Ib), Formula (Ic), and Formula (II), there is a further embodiment wherein all variables are as defined for the embodiment in question, except that $R_4$ is selected from the group of H and $C_1$-$C_6$ alkyl.

Within each of the embodiments described herein for a compound of Formula (I), Formula (Ia), Formula (Ib), Formula (Ic), and Formula (II), there is a further embodiment wherein all variables are as defined for the embodiment in question, except that $R_4$ is H.

Within each of the embodiments described herein for a compound of Formula (I), Formula (Ia), Formula (Ib), Formula (Ic), and Formula (II), there is a further embodiment wherein all variables are as defined for the embodiment in question, except that $R_4$ is $C_1$-$C_6$ alkyl.

Within each of the embodiments described herein for a compound of Formula (I), Formula (Ia), Formula (Ib), Formula (Ic), and Formula (II), there is a further embodiment wherein all variables are as defined for the embodiment in question, except that $R_4$ is $C_1$-$C_4$ alkyl.

Methods of Use

The compounds described herein, including a pharmaceutically acceptable salt, pharmaceutically acceptable co-crystal, pharmaceutically acceptable ester, pharmaceutically acceptable solvate, hydrate, isomer (including optical isomers, racemates, or other mixtures thereof), tautomer, isotope, polymorph, or a pharmaceutically acceptable prodrug thereof, may be used in methods of medical treatment associated with renervation.

In some embodiments, the methods concern renervation in the peripheral nervous system, including those associated with or caused by traumas (including physical, chemical, and thermal traumas), surgery, compressions, and diseases or disorders affecting the nerves. Included are ulnar nerve injuries, radial nerve injuries, median nerve injuries, musculocutaneous nerve injuries, axillary nerve injuries, suprascapular nerve injuries, thoracodorsal nerve injuries, long thoracic nerve injuries, dorsal scapular nerve injuries, phrenic nerve injuries, superior gluteal nerve injuries, inferior gluteal nerve injuries, femoral nerve injuries, lateral femoral cutaneous nerve injuries (meralgia paresthetica), obturator nerve injuries, sciatic nerve injuries, tibial nerve injuries, common peroneal nerve injuries, anterior interosseous nerve injuries, and sural nerve lesions.

Injuries to the nerves and nerve tissues of both the central and peripheral nervous systems may result from traction injuries (stretch-related injuries), lacerations, compressions/crush injuries, and thermal damage. Peripheral nerve damage considered herein includes neruapraxia, axonotmesis, and neurotmesis.

Injuries to the central nervous system may include spinal cord injuries, traumatic brain injuries, inflammatory nerve damage, nerve damage resulting from vascular disorders (stroke, ischemia, transient ischemic attack (TIA), subarachnoid hemorrhage, subdural hemorrhage and hematoma, and extradural hemorrhage), infections (including meningitis, encephalitis, polio, and epidural abscesses), and brain or spinal cord tumors.

The renervation may be accomplished following a physical trauma to the nerves, including those from falls, vehicle accidents, battlefield injuries, violence, workplace and sports injuries, and the like. The renervation may also be accomplished following physical trauma to nerves associated with medical procedures, including surgeries, amputations, radiation treatments, and implantation of medical devices or prosthetics.

The renervation may be accomplished following chemical trauma to nerves, such as that caused by medications, drug abuse or overdose, alcohol abuse or overdose, chemotherapies, carbon dioxide or carbon monoxide poisoning, exposure to herbicides, insecticides, rodenticides, heavy metals, neurotoxins, or other toxic chemicals and biochemicals.

"Trk receptors" are a family of tyrosine kinases referred to as Tropomyosin receptor kinases, particularly including Tropomyosin receptor kinase A (Trk A), Tropomyosin receptor kinase B (Trk B), and Tropomyosin receptor kinase C (Trk C).

Definitions

Also understood to be included herein for a compound of Formula I, for a compound of each of the other Formulas, and for the individual compounds taught herein, are the pharmaceutically acceptable salts, pharmaceutically acceptable co-crystals, pharmaceutically acceptable esters, pharmaceutically acceptable solvates, hydrates, isomers (including optical isomers, racemates, or other mixtures thereof), tautomers, isotopes, polymorphs, and pharmaceutically acceptable prodrugs of such compounds. In instance wherein, for brevity, reference is made only to one or more pharmaceutically acceptable salts of a compound, the inclusion of pharmaceutically acceptable co-crystals, pharmaceutically acceptable esters, pharmaceutically acceptable solvates, hydrates, isomers (including optical isomers, racemates, or other mixtures thereof), tautomers, isotopes, polymorphs, and pharmaceutically acceptable prodrugs of such compounds is understood.

The term "denervation" refers to the loss of nerve supply or nerve function, including that caused by trauma, disease, chemical toxicity, and surgical intervention. The term "renervation" refers to the resupply of one or more nerves, nerve tissues, and/or nerve activity. In different embodiments, the renervation may comprise a resupply of one or more nerves, nerve tissues, and/or nerve activity in an area of damage or scarring caused, respectively, by each of the injuries, traumas, diseases (such as diabetes, cardiac ischemia, peripheral artery/vascular disease, myocarditis, idiopathic cardiomyopathy, infections), disorders, or other causes described herein and others known in the art to result in denervation in a subject.

A "traumatic brain injury" or "intracranial injury" is any injury that disrupts normal brain function(s), including those caused by bumps, blows, concussions, or jolts to the head, as well as penetrating head injuries. A "spinal cord injury" refers to any injury causing damage and/or loss of function to the spinal cord or the nerves of the spinal canal (cauda equine). Such spinal injuries include those caused by motor vehicle accidents, whiplash, falls, sports and recreation accidents, and diseases including cancer, arthritis, osteoporosis and inflammation of the spinal cord.

The term "variable" as used in the generic chemical descriptions herein refers to a chemical element, atom, group, moiety, integer, or the like, for which there are more than one variable options defined. For instance, each of $R_1$, $R_2$, $R_3$, $R_4$, $R_5$, $R_a$, $R_b$, n1, n2, n3, n4, and n5 represent variables in the chemical definitions.

All ranges disclosed and/or claimed herein are inclusive of the recited endpoint and independently combinable. For example, the ranges of "from 2 to 10" and "2-10" are inclusive of the endpoints, 2 and 10, and all the intermediate values between in context of the units considered. For instance, reference to "Claims 2-10" or "$C_2$-$C_{10}$ alkyl" includes units 2, 3, 4, 5, 6, 7, 8, 9, and 10, as claims and atoms are numbered in sequential numbers without fractions or decimal points, unless described in the context of an average number. The context of "pH of from 5-9" or "a temperature of from 5° C. to 9° C.", on the other hand, includes whole numbers 5, 6, 7, 8, and 9, as well as all fractional or decimal units in between, such as 6.5 and 8.24.

The term "therapeutically effective amount" or "pharmaceutically effective amount" refers to an amount that is sufficient to effect a method of treatment, as described herein, when administered to a subject (e.g., a mammal, such as a human) in need of such treatment. The therapeutically or pharmaceutically effective amount will vary depending upon the subject and disease condition being treated, the weight and age of the subject, the severity of the disease condition, the manner of administration and the like, which can readily be determined by one of ordinary skill in the art. For example, a "therapeutically effective amount" or a "pharmaceutically effective amount" of a compound of Formula I, or a pharmaceutically acceptable salt or co-crystal thereof, is an amount sufficient to promote cardiac sympathetic nerve regeneration, and thereby treat a subject (e.g., a human) suffering an indication, such as denervation, or to ameliorate or alleviate the existing symptoms of the indication. For example, a therapeutically or pharmaceutically effective amount may be an amount sufficient to decrease a symptom of a disease or condition responsive to inhibition of the interaction between protein tyrosine phosphatase receptor sigma (PTPσ) and receptors from the Trk receptor family (TrkA, TrkB, and TrkC).

In some embodiments, a pharmaceutically or therapeutically effective amount or a single dosage unit contains from 0.1 mg to 1 g, 0.1 mg to 100 mg, 0.1 mg to 200 mg, 0.1 mg to 300 mg, 0.1 mg to 400 mg, 0.1 mg to 500 mg, 0.1 mg to 600 mg, 0.1 mg to 700 mg, 0.1 mg to 800 mg, 0.1 mg to 900 mg, or 0.1 mg to 1,000 mg of a compound of Formula I, or a pharmaceutically acceptable salt or co-crystal thereof (or a compound of another Formula or a specific compound described herein). In some embodiments, a therapeutically effective amount or a pharmaceutically effective amount of a compound of Formula (I), or a pharmaceutically acceptable salt thereof, comprises from about 0.1 mg to about 500 mg per dose, given once or twice daily. In some embodiments, the individual dose is selected from 1 mg, 5 mg, 10 mg, 20 mg, 30 mg, 40 mg, 50 mg, 60 mg, 75 mg, 100 mg, 150 mg, 200 mg, 250 mg, 300 mg, 350 mg, 400 mg, and 500 mg per dose.

The terms "branched" or "branching" in reference to hydrocarbon chains, including alkyl, alkenyl, and alkynyl chains, with or without cyclic groups in the chain, refers to a carbon chain of carbon atoms with branches of one or more additional carbon chains of at least one carbon atom extending therefrom. Non-limiting examples of branched or branching carbon chains include 2-methylbutyl and 2-ethylpent-3-en-1-yl chains. Non-limiting examples of branched or branching carbon chains as substituents include isopropyl, isobutyl, 2-methylbutyl, sec-butyl, and tert-butyl groups.

The term "alkyl" refers to a straight or branched hydrocarbon. For example, an alkyl group can include those having 1 to 10 carbon atoms (i.e, $C_1$-$C_{10}$ alkyl), 1 to 8 carbon atoms (i.e., $C_1$-$C_8$ alkyl), or 1 to 4 carbon atoms (i.e., $C_1$-$C_6$ alkyl). Examples of suitable alkyl groups include, but are not limited to, methyl, ethyl, n-propyl, isopropyl ($—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)$ $_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$, octyl ($-(CH_2)_7CH_3$), nonyl ($-(CH_2)_8CH_3$), and decyl ($-(CH_2)_9CH_3$) groups.

Unless otherwise stipulated otherwise, reference herein to an alkyl chain of three or more carbon atoms is understood to allow for straight (linear) alkyl chains and branched alkyl chains of the indicated number or number range of carbon atoms.

The term "alkoxy" refers to a group having the formula —O-alkyl, in which an alkyl group, as defined above, is attached to the parent molecule via an oxygen atom. The alkyl portion of an alkoxy group can have 1 to 10 carbon atoms (i.e., $C_1$-$C_{10}$ alkoxy), 1 to 8 carbon atoms (i.e., $C_1$-$C_8$ alkoxy), or 1 to 6 carbon atoms (i.e., $C_1$-$C_6$ alkoxy). Examples of suitable alkoxy groups include, but are not limited to, methoxy ($-O-CH_3$ or —OMe), ethoxy ($-OCH_2CH_3$ or —OEt), t-butoxy ($-O-C(CH_3)_3$ or —OtBu) and the like.

The term "halogen" or "halo" refers to F, Cl, Br, or I.

The term "haloalkyl" refers to an alkyl group, as defined above, in which one or more hydrogen atoms of the alkyl group is replaced with a halogen atom. The alkyl portion of a haloalkyl group can have, for instance, 1 to 4 carbon atoms (i.e., $C_1$-$C_4$ haloalkyl), 1 to 3 carbon atoms (i.e., $C_1$-$C_3$ haloalkyl), or 1 to 2 carbon atoms (i.e., $C_1$-$C_2$ haloalkyl). Non-limiting examples of suitable haloalkyl groups, which may also be referred to as halofluoro groups include, but are not limited to, trifluoromethyl ($-CF_3$), difluoromethyl ($-CHF_2$), fluoromethyl ($-CFH_2$), 2-fluoroethyl ($-CH_2CH_2F$), 2-fluoropropyl ($-CH_2CHF_2$), 2,2,2-trifluoroetheyl ($-CH_2CF_3$), 1,1-difluoroethyl ($-CF_2CH_3$), 2-fluoropropyl ($-CH_2CHFCH_3$), 1,1-difluoropropyl ($-CF_2CH_2CH_3$), 2,2-difluoropropyl ($-CH_2CF_2CH_3$), 3,3-difluoropropyl ($-CH_2CH_2CHF_2$), 3,3,3-trifluoropropyl ($-CH_2CH_2CHF_3$), 1,1-difluorobutyl ($-CF_2CH_2CH_2CH_3$), perfluoroethyl ($-CF_2CF_3$), perfluoropropyl ($-CF_2CF_2CF_3$), 1,1,2,2,3,3-hexafluorobutyl ($-CF_2-CF_2CF_2CH_3$), perfluorobutyl ($-CF_2CF_2CF_2CF_3$), 1,1,1,3,3,3-hexafluoropropan-2-yl ($-CH_2(CF_3)2$) groups, and the like. Additional groups wherein the halogen substitution is with bromine, iodine, or chlorine atoms are also understood for use herein.

The term "heterocycle" or "heterocyclyl" as used herein includes by way of example and not limitation those heterocycles described in Paquette, Leo A.; Principles of Modern Heterocyclic Chemistry (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, and tetrazolyl rings. A 4-membered to 6-membered (4- to 6-membered) heterocycle refers to a ring having 4, 5, or 6 ring atoms, at least one of which is not a ring carbon atom.

The terms "heteroaromatic" and "heteroaryl" refer to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

Methods

General Chemistry Methods

The compounds herein, as well as the pharmaceutically acceptable salts, pharmaceutically acceptable co-crystals, pharmaceutically acceptable esters, pharmaceutically acceptable solvates, hydrates, isomers (including optical isomers, racemates, or other mixtures thereof), tautomers, isotopes, polymorphs, and pharmaceutically acceptable prodrugs thereof may be prepared by methods known in the art, including those described herein.

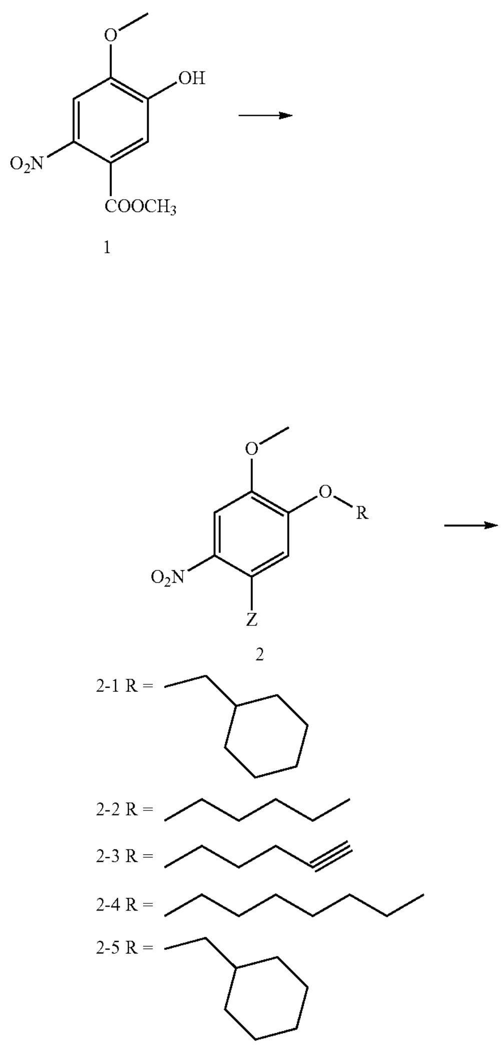

-continued

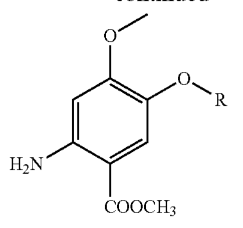

3

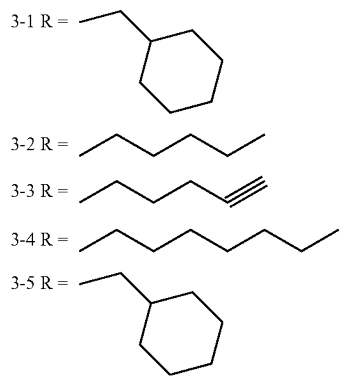

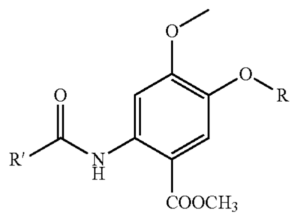

4

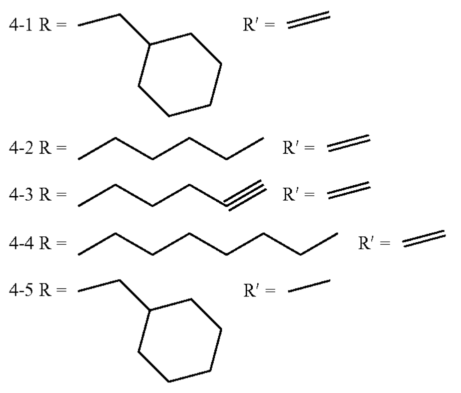

-continued

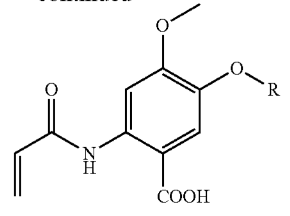

5

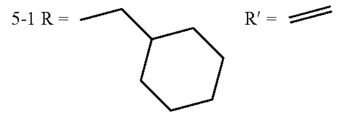

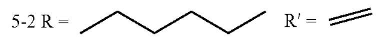

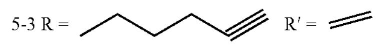

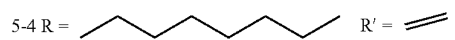

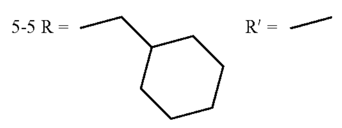

Methyl 5-(cyclohexylmethoxy)-4-methoxy-2-nitrobenzoate (2-1)

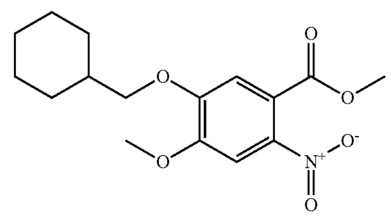 [SMILES: COC(=O)c1cc(OCC2CCCCC2)c(OC)cc1[N+](=O)[O-]]

To a solution of methyl 5-hydroxy-4-methoxy2-nitrobenzoate (227 mg, 1.0 mmol) in DMF (10 mL) was added $K_2CO_3$ (207 mg, 1.5 mmol) and cyclohexylmethyl bromide (212 mg, 1.2 mmol). The reaction mixture was heated to 100° C. and stirred for 10 hr. After the reaction was over, the mixture was cooled to room temperature. The mixture was then filtered to remove the inorganic material. Filtrate was diluted with water (5 mL) and extracted with ethyl acetate (3×10 ml). The combined organic layers were washed with water (3×10 mL) and dried over anhydrous sodium sulfate. Removal of solvent under vacuo gave the residue which was chromatographed on silica gel with EtOAc:Hexane (1:4 v/v) as eluent to give 293 mg (yield 91%) desired product. $^1H$ NMR (400 MHz, Chloroform-d) δ $^1H$ NMR (400 MHz, Chloroform-d) δ 7.44 (s, 1H), 7.02 (s, 1H), 3.94 (s, 3H), 3.89 (s, 3H), 3.87 (d, J=6.3 Hz, 2H), 1.87-1.74 (m, 6H), 1.37-1.14 (m, 3H), 1.12-0.90 (m, 2H). $^{13}C$ NMR (101 MHz, $CDCl_3$) δ 166.62, 152.60, 150.69, 140.80, 121.85, 111.67, 107.23, 75.09, 56.66, 53.33, 37.37, 29.83, 26.46, 25.70.

Methyl 2-amino-5-(cyclohexylmethoxy)-4-methoxybenzoate (3-1)

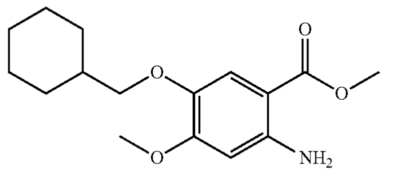 [SMILES: COC(=O)c1cc(OCC2CCCCC2)c(OC)cc1N]

To a solution of Methyl 5-(cyclohexylmethoxy)-4-methoxy-2-nitrobenzoate (2) (260 mg, 0.8 mmol) in anhydrous MeOH was added Pd/C (10 wt %, 55 mg). The mixture was stirred under $H_2$ atmosphere for 4 hours before it was filtered through a pad of celite. The solvent was removed in vacuo and the residue was purified by flash column chromatography to afford 218 mg (93%) of the desired product. $^1$H NMR (400 MHz, Chloroform-d) δ 7.29 (s, 1H), 6.12 (s, 1H), 5.57 (s, 2H), 3.88 (s, 3H), 3.83 (s, 3H), 3.71 (d, J=6.4 Hz, 2H), 1.91-1.69 (m, 6H), 1.34-1.15 (m, 3H), 1.01 (m, 2H). $^{13}$C NMR (101 MHz, $CDCl_3$) δ 168.30, 155.67, 147.22, 140.33, 115.21, 102.23, 99.50, 75.66, 55.83, 51.40, 37.76, 30.09, 26.68, 25.88

Methyl 2-acrylamido-5-(cyclohexylmethoxy)-4-methoxybenzoate (4-1)

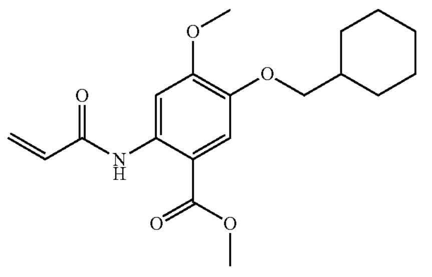 [SMILES: C=CC(=O)Nc1cc(OC)c(OCC2CCCCC2)cc1C(=O)OC]

Methyl 2-amino-5-(cyclohexylmethoxy)-4-methoxybenzoate (3) (205 mg, 0.7 mmol) was dissolved in DCM (5 mL) followed by addition of acryloyl chloride (76 mg, 0.84 mmol) at 0° C. Triethylamine (84 mg, 0.84 mmol) was then syringed into the reaction mixture and the solution was stirred for 4 hour and allowed to warm to ambient temperature. The reaction was concentrated and redissolved in EtOAc. The organic solution was then washed with water, saturated sodium bicarbonate, and brine. The organic layer was dried over magnesium sulfate, filtered, concentrated, and purified by column chromatography (1:4) EtOAc: Hexanes) to deliver 221 mg (yield 91%) desired product. $^1$H NMR (400 MHz, Chloroform-d) δ 11.39 (s, 1H), 8.56 (s, 1H), 7.44 (s, 1H), 6.41-6.24 (m, 2H), 5.77 (dt, J=10.0, 1.6 Hz, 1H), 3.95 (s, 3H), 3.93 (s, 3H), 3.77 (dd, J=6.4, 1.8 Hz, 2H), 1.96-1.64 (m, 6H), 1.38-1.11 (m, 3H), 1.11-0.96 (m, 2H). $^{13}$C NMR (101 MHz, $CDCl_3$) δ 168.67, 164.16, 154.75, 143.92, 137.66, 132.53, 127.28, 114.11, 106.74, 75.00, 56.22, 52.25, 37.68, 30.08, 26.65, 25.86.

2-acrylamido-5-(cyclohexylmethoxy)-4-methoxybenzoic Acid (5-1, HJ-01)

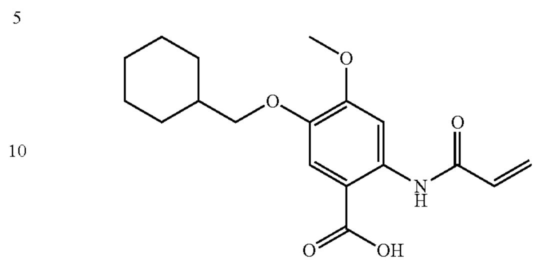

Methyl 2-acrylamido-5-(cyclohexylmethoxy)-4-methoxybenzoate (4-1) (20 mg, 0.058 mmol) was dissolved in THF (1 mL) followed by 2M LiOH (0.12 ml, 0.24 mmol) and the mixture was stirred at r.t. overnight. After the reaction was over, acidify the mixture with 1N HCl and the product was extracted with ethyl acetate to afford 16 mg product. Yield: 85%.

1H NMR (400 MHz, Chloroform-d) δ 8.46 (s, 1H), 7.55 (s, 1H), 6.40-6.30 (m, 2H), 5.81 (dd, J=9.2, 2.2 Hz, 1H), 4.62 (s, 15H), 3.96 (s, 3H), 3.81 (d, J=6.3 Hz, 2H), 1.96-1.87 (m, 3H), 1.82-1.73 (m, 3H), 1.39-1.19 (m, 3H), 1.08 (t, J=11.9 Hz, 2H). $^{13}$C NMR (101 MHz, $CDCl_3$) δ 169.80, 164.22, 153.89, 143.55, 136.60, 131.85, 126.75, 114.74, 107.48, 103.28, 74.59, 55.48, 37.22, 29.50, 26.10, 25.34.

Methyl 5-(hexyloxy)-4-methoxy-2-nitrobenzoate (2-2)

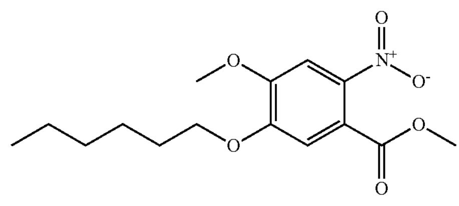 [SMILES: CCCCCCOc1cc(C(=O)OC)c([N+](=O)[O-])cc1OC]

To a solution of methyl 5-hydroxy-4-methoxy2-nitrobenzoate (227 mg, 1.0 mmol) in DMF (10 mL) was added $K_2CO_3$ (207 mg, 1.5 mmol) and bromohexane (198 mg, 1.2 mmol). The reaction mixture was heated to 100° C. and stirred for 10 hr. After the reaction was over, the mixture was cooled to room temperature. The mixture was then filtered to remove the inorganic material. Filtrate was diluted with water (5 mL) and extracted with ethyl acetate (3×10 ml). The combined organic layers were washed with water (3×10 mL) and dried over anhydrous sodium sulfate. Removal of solvent under vacuo gave the residue which was chromatographed on silica gel with EtOAc:Hexane (1:4 v/v) as eluent to give 286 mg (yield 92%) desired product. $^1$H NMR (400 MHz, Chloroform-d) $\delta_H$ (ppm)=$^1$H NMR (400 MHz, Chloroform-d) δ 7.45 (s, 1H), 7.05 (s, 1H), 4.09 (t, J=6.8 Hz, 2H), 3.95 (s, 3H), 3.90 (s, 3H), 1.87 (p, J=6.9 Hz, 2H), 1.45 (m, 2H), 1.34 (m, 4H), 0.95-0.86 (m, 3H). $^{13}$C NMR (101 MHz, $CDCl_3$) $\delta_C$ (ppm)=166.61, 152.39, 150.65, 140.95, 121.85, 111.68, 107.22, 69.91, 56.68, 53.38, 31.57, 28.90, 25.62, 22.67, 14.14.

Methyl 2-amino-5-(hexyloxy)-4-methoxybenzoate (3-2)

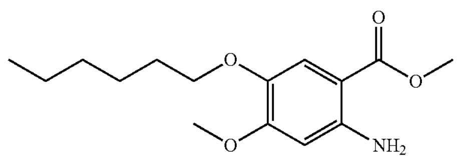 [SMILES: CCCCCCOc1cc(C(=O)OC)c(N)cc1OC]

To a solution of methyl 5-(hexyloxy)-4-methoxy-2-nitrobenzoate (250 mg, 0.8 mmol) in anhydrous MeOH was added Pd/C (10 wt %, 55 mg). The mixture was stirred under $H_2$ atmosphere for 4 hours before it was filtered through a pad of celite. The solvent was removed in vacuo and the residue was purified by flash column chromatography to afford 202 mg (90%) of the desired product. $^1$H NMR (400 MHz, Chloroform-d) $\delta_H$ (ppm)=7.31 (s, 1H), 6.13 (s, 1H), 5.57 (br, 2H), 3.91 (t, J=6.9 Hz, 2H), 3.84 (s, 6H), 1.79 (t, J=7.6 Hz, 2H), 1.52-1.39 (m, 2H), 1.34 (m, 4H), 0.91 (d, J=7.0 Hz, 3H). $^{13}$C NMR (101 MHz, $CDCl_3$) $\delta_C$ (ppm) =168.33, 155.56, 147.23, 140.08, 115.08, 102.30, 99.48, 70.06, 55.87, 51.44, 31.75, 29.38, 25.79, 22.79, 14.18.

Methyl 2-acrylamido-5-(hexyloxy)-4-methoxybenzoate (4-2)

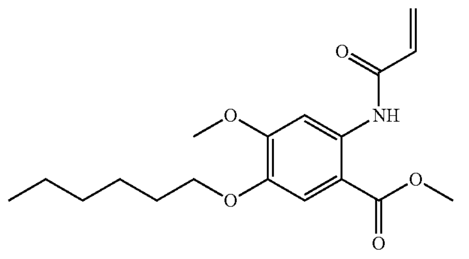 [SMILES: C=CC(=O)Nc1cc(OC)c(OCCCCCC)cc1C(=O)OC]

Methyl 2-amino-5-(hexyloxy)-4-methoxybenzoate (3-2) (197 mg, 0.7 mmol) was dissolved in DCM (5 mL) followed by addition of acryloyl chloride (76 mg, 0.84 mmol) at 0° C. Triethylamine (84 mg, 0.84 mmol) was then syringed into the reaction mixture and the solution was stirred for 4 hour and allowed to warm to ambient temperature. The reaction was concentrated and redissolved in EtOAc. The organic solution was then washed with water, saturated sodium bicarbonate, and brine. The organic layer was dried over magnesium sulfate, filtered, concentrated, and purified by column chromatography EtOAc:Hexanes (1:4) to deliver 211 mg (yield 90%) desired product. $^1$H NMR (400 MHz, Chloroform-d) $\delta_H$ (ppm)=11.40 (s, 1H), 8.57 (s, 1H), 7.47 (s, 1H), 6.58-6.23 (m, 2H), 5.77 (dd, J=10.0, 1.4 Hz, 1H), 4.00 (t, J=6.8 Hz, 2H), 3.96 (s, 3H), 3.90 (s, 3H), 1.83 (p, J=7.0 Hz, 2H), 1.59 -1.38 (m, 2H), 1.40-1.21 (m, 4H), 1.02-0.77 (m, 3H). $^{13}$C NMR (101 MHz, $CDCl_3$) $\delta_C$ (ppm)=168.66, 164.18, 154.64, 143.64, 137.72, 132.52, 127.31, 113.99, 106.76, 103.68, 69.51, 56.23, 52.25, 31.71, 29.83, 29.22, 25.76, 22.71, 14.17.

2-acrylamido-5-(hexyloxy)-4-methoxybenzoic Acid (5-2, HJ-02)

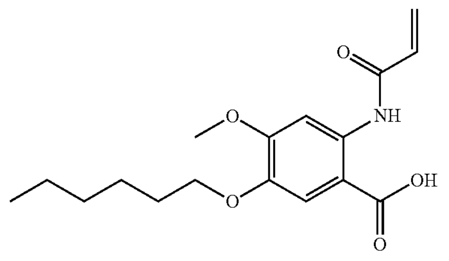 [SMILES: C=CC(=O)Nc1cc(OC)c(OCCCCCC)cc1C(=O)O]

Methyl 2-acrylamido-5-(hexyloxy)-4-methoxybenzoate (4-2) (20 mg, 0.06 mmol) was dissolved in THF (1 mL) followed by 2M LiOH (0.12 ml, 0.24 mmol) and the mixture was stirred at r.t. overnight. After the reaction was over, acidify the mixture with 1N HCl and the product was extracted with ethyl acetate to afford 15 mg product. Yield: 80%.

$^1$H NMR (400 MHz, Methanol-$d_4$) $\delta_H$ (ppm)=11.17 (s, 1H), 8.61 (d, J=0.9 Hz, 1H), 7.55 (d, J=1.0 Hz, 1H), 6.60-6.14 (m, 2H), 5.81 (dt, J=10.0, 1.1 Hz, 1H), 4.03 (t, J=6.8 Hz, 2H), 3.99 (s, 3H), 1.85 (p, J=7.0 Hz, 2H), 1.60 -1.42 (m, 2H), 1.36 (m, 4H), 0.91 (t, J=6.0 Hz, 3H). $^{13}$C NMR (101 MHz, $CDCl_3$) $\delta_C$ (ppm)=172.36, 164.12, 155.51, 143.74, 138.38, 132.21, 127.67, 114.39, 105.45, 72.83, 69.37, 56.23, 31.58, 29.05, 25.63, 22.59, 14.05.

Methyl 5-(hex-5-yn-1-yloxy)-4-methoxy-2-nitrobenzoate (2-3)

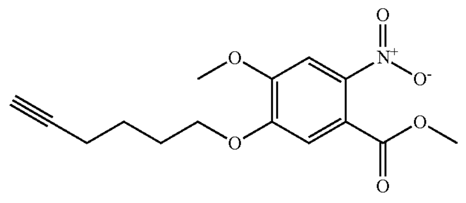 [SMILES: C#CCCCCOc1cc(C(=O)OC)c([N+](=O)[O-])cc1OC]

To a solution of methyl 5-hydroxy-4-methoxyl-nitrobenzoate (227 mg, 1.0 mmol) in DMF (10 mL) was added $K_2CO_3$ (207 mg, 1.5 mmol), KI (33 MCl, 0.2 mmol) and 6-chloro-1-hexyne (140 mg, 1.2 mmol). The reaction mixture was heated to 120° C. and stirred for 15 hr. After the reaction was over, the mixture was cooled to room temperature. The mixture was then filtered to remove the inorganic material. Filtrate was diluted with water (5 mL) and extracted with ethyl acetate (3×10 ml). The combined organic layers were washed with water (3×10 mL) and dried over anhydrous sodium sulfate. Removal of solvent under vacuo gave the residue which was chromatographed on silica gel with EtOAc:Hexane (1:4 v/v) as eluent to give 270 mg (yield 88%) desired product. $^1$H NMR (400 MHz, Chloroform-d) δ 7.45 (s, 1H), 7.06 (s, 1H), 4.13 (t, J=6.4 Hz, 2H), 3.95 (s, 3H), 3.90 (s, 3H), 2.29 (td, J=7.0, 2.6 Hz, 2H), 2.12-1.89 (m, 3H), 1.80-1.63 (m, 2H). $^{13}$C NMR (101 MHz, $CDCl_3$) δ 166.49, 152.15, 150.70, 141.13, 121.73, 111.75, 107.23, 83.82, 69.19, 69.07, 56.66, 53.37, 27.91, 24.88, 18.19.

Methyl 2-amino-5-(hex-5-yn-1-yloxy)-4-methoxy-benzoate (3-3)

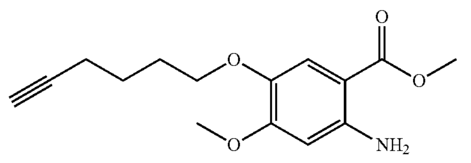 [SMILES: C#CCCCCOc1cc(C(=O)OC)c(N)cc1OC]

To a solution of methyl 5-(hex-5-yn-1-yloxy)-4-methoxy-2-nitrobenzoate (247 mg, 0.8 mmol) in anhydrous MeOH was added Pd/C (10 wt %, 55 mg). The mixture was stirred under $H_2$ atmosphere for 4 hours before it was filtered through a pad of celite. The solvent was removed in vacuo and the residue was purified by flash column chromatography to afford 200 mg (90%) of the desired product. $^1$H NMR (400 MHz, Chloroform-d) δ 7.32 (s, 1H), 6.13 (s, 1H), 5.58 (br, 2H), 3.96 (t, J=Hz, 2H), 3.84 (s, 6H), 2.28 (m, 2H), 1.99-1.85 (m, 3H), 1.73 (m, 2H). $^{13}$C NMR (101 MHz, $CDCl_3$) δ 168.30, 155.64, 147.40, 139.93, 115.42, 102.30, 99.50, 84.36, 69.58, 68.68, 55.88, 51.47, 28.48, 25.20, 18.32.

Methyl 2-acrylamido-5- (hex-5-yn-1-yloxy)-4-methoxybenzoate (4-3)

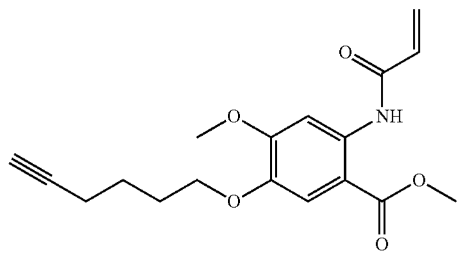 [SMILES: C#CCCCCOc1cc(C(=O)OC)c(NC(=O)C=C)cc1OC]

Methyl 2-amino-5-(hex-5-yn-1-yloxy)-4-methoxybenzoate (4-2) (194 mg, 0.7 mmol) was dissolved in DCM (5 mL) followed by addition of acryloyl chloride (76 mg, 0.84 mmol) at 0° C. Triethylamine (84 mg, 0.84 mmol) was then syringed into the reaction mixture and the solution was stirred for 4 hour and allowed to warm to ambient temperature. The reaction was concentrated and redissolved in EtOAc. The organic solution was then washed with water, saturated sodium bicarbonate, and brine. The organic layer was dried over magnesium sulfate, filtered, concentrated, and purified by column chromatography (1:4) EtOAc: Hexanes) to deliver 207 mg (yield 89%) desired product. $^1$H NMR (400 MHz, Chloroform-d) δ 11.40 (s, 1H), 8.58 (s, 1H), 7.48 (s, 1H), 6.61-6.16 (m, 2H), 5.89-5.63 (m, 1H), 4.03 (t, J=6.4 Hz, 2H), 3.96 (s, 3H), 3.91 (s, 3H), 2.29 (m, 2H), 1.97 (m, 3H), 1.81-1.68 (m, 2H). $^{13}$C NMR (101 MHz, $CDCl_3$) δ 168.63, 164.23, 154.71, 143.50, 137.90, 132.51, 127.38, 114.30, 106.78, 103.74, 84.20, 68.89, 68.80, 56.24, 52.28, 28.30, 25.12, 18.30.

2-acrylamido-5-(hex-5-yn-1-yloxy)-4-methoxybenzoic Acid (5-3)

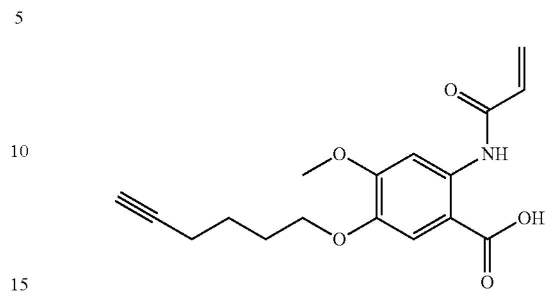

Methyl 2-acrylamido-5-(hex-5-yn-1-yloxy)-4-methoxybenzoate (5-2) was dissolved in THF (1 mL) followed by 2M LiOH (0.12 ml, 0.24 mmol) and the mixture was stirred at r.t. overnight. After the reaction was over, acidify the mixture with 1N HCl and the product was extracted with ethyl acetate to afford 16 mg product. Yield: 85%. $^1$H NMR (400 MHz, Chloroform-d) δ 8.51 (s, 1H), 7.57 (s, 1H), 6.58-6.22 (m, 2H), 5.79 (dd, J=9.8, 1.5 Hz, 1H), 4.06 (t, J=6.5 Hz, 2H), 3.96 (s, 3H), 2.29 (td, J=7.1, 2.7 Hz, 2H), 2.05-1.91 (m, 3H), 1.82-1.67 (m, 2H). $^{13}$C NMR (101 MHz, $CDCl_3$) δ 170.28, 164.40, 154.26, 143.40, 137.32, 132.51, 127.30, 114.99, 107.56, 103.57, 84.08, 68.78, 68.69, 55.99, 28.13, 24.96, 18.11.

2-acrylamido-4-methoxy-5-(octyloxy)benzoic Acid (5-4)

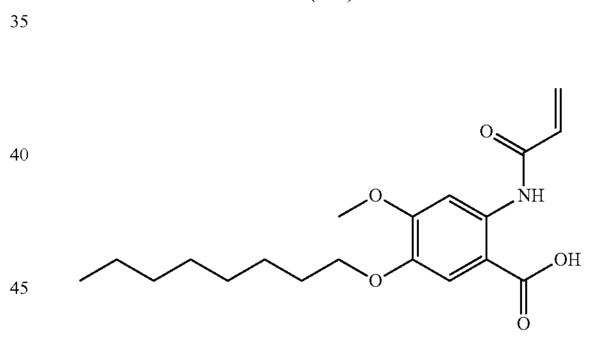

Methyl 2-acrylamido-5-(octyloxy)-4-methoxy benzoate (4) was dissolved in THF (1 mL) followed by 2M LiOH (0.12 ml, 0.24 mmol) and the mixture was stirred at r.t. overnight. After the reaction was over, acidify the mixture with 1N HCl and the product was extracted with ethyl acetate to afford 16 mg product. Yield: 85%. $^1$H NMR (400 MHz, Chloroform-d) δ 11.19 (s, 1H), 8.61 (s, 1H), 7.54 (s, 1H), 6.46-6.28 (m, 2H), 5.81 (dd, J=10.0, 1.4 Hz, 1H), 4.07-3.93 (m, 5H), 1.95-1.72 (m, 2H), 1.46 (m, 2H), 1.37-1.22 (m, 11H), 1.00-0.71 (m, 3H). $^{13}$C NMR δ (101 MHz, $CDCl_3$) δ 171.79, 164.24, 155.58, 143.84, 138.53, 132.38, 127.74, 114.54, 105.52, 103.76, 69.53, 56.37, 31.95, 29.50, 29.36, 29.24, 26.09, 22.81, 14.27.

5-(cyclohexylmethoxy)-4-methoxy-2-propionamido-benzoic Acid (5-5)

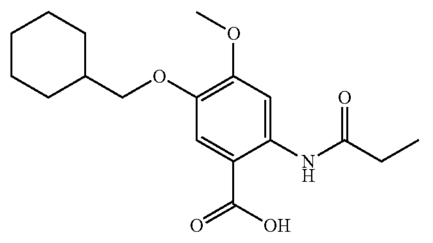 [SMILES: CCC(=O)Nc1cc(OC)c(OCC2CCCCC2)cc1C(=O)O]

Methyl 5-(cyclohexylmethoxy)-4-methoxy-2-propionamidobenzoate was dissolved in THF (1 mL) followed by 2M LiOH (0.12 ml, 0.24 mmol) and the mixture was stirred at r.t. overnight. After the reaction was over, acidify the mixture with 1N HCl and the product was extracted with ethyl acetate to afford 16 mg product. Yield: 85%. $^1$H NMR (400 MHz, DMSO-$d_6$) δ 8.32 (s, 1H), 7.39 (s, 1H), 3.80 (s, 3H), 3.72 (d, J=6.4 Hz, 2H), 2.39 (q, J=7.5 Hz, 2H), 1.92-1.57 (m, 6H), 1.35-1.16 (m, 3H), 1.12 (t, J=7.5 Hz, 3H), 1.03 (td, J=11.8, 11.4, 3.2 Hz, 2H). $^{13}$C NMR (101 MHz, DMSO) δ 171.77, 169.37, 153.46, 142.79, 136.96, 114.04, 107.26, 103.12, 73.69, 55.58, 37.19, 30.72, 29.29, 26.08, 25.26, 9.38.

Animals and Treatment Groups:

C57BL/6J mice and pregnant Sprague Dawley rats were obtained from Jackson Laboratories West (Sacramento, CA). All mice and rats were kept on a 12 h:12 h light-dark cycle with ad libitum access to food and water. Age and gender-matched male and female mice 12-18 weeks old were used for surgeries, while ganglia from male and female neonatal rats were used for explants and dissociated cultures. All procedures were approved by the OHSU Institutional Animal Care and Use Committee and comply with the Guide for the Care and Use of Laboratory Animals published by the National Academies Press ($8^{th}$ edition).

Treatment groups: Mice received daily subcutaneous injections on days 3-10 after ischemia-reperfusion or sham surgery with HJ-01 (10 mg/kg), HJ-02 (10 mg/kg), ISP (intracellular sigma peptide; 10 μmol), or DMSO vehicle (5% DMSO/PBS). Unless otherwise noted, six mice/group were analyzed.

Myocardial Ischemia-Reperfusion:

Myocardial infarction was generated by ischemia-reperfusion as described previously[11]. Anesthesia was induced with 4% isoflurane and maintained with 2% isoflurane. The left anterior descending coronary artery (LAD) was reversibly ligated for 30 min and then reperfused by release of the ligature. Occlusion was confirmed by sustained S-T wave elevation and regional cyanosis. Reperfusion was confirmed by the return of color to the ventricle distal to the ligation and reperfusion arrhythmia. Core body temperature was monitored by a rectal probe and maintained at 37° C., and a two-lead electrocardiogram was monitored. Sham surgery: Sham animals underwent the procedure described above, except for the LAD ligature.

In Vivo Telemetry:

ECGs were obtained from conscious adult mice using ETA-F10 (Data Sciences International) telemetry implants and analyzed with the Dataquest ART software (Data Sciences International) as described previously[13]. Mice were anaesthetized with 4% and maintained on 2% inhaled isoflurane. A transmitter was implanted subcutaneously in a lead II configuration, with the negative lead placed in the right pectoral muscle and the positive lead to the left of the xyphoid process. Devices were implanted at least 5 days before I-R or sham surgery. ECG recordings were obtained 14 days after sham or MI surgery. ECGs were analyzed beginning 60 min before IP injection of a relatively low dose of the β-AR agonist isoproterenol (ISO, 10 μg or ~0.5 mg/kg) as a baseline, and then for 60 min after injection to identify ISO-induced arrhythmias. PVCs were defined as a single premature QRS complex in the absence of a P-wave. Heart rate was analyzed to confirm that the SA node response to ISO was similar between groups.

Echocardiography

High-frequency fundamental imaging (Vevo 2100) was performed at 25 to 40 MHz depending on the echocardiographic data that were acquired. Mice were sedated with inhaled isoflurane (1.0%-1.5%). Images were obtained in the parasternal long-axis plane and parasternal short-axis planes at the midpapillary level. Measurement of left ventricular (LV) end-diastolic and end-systolic area (short axis) and end-diastolic and end-systolic length (long axis) were used to measure LV function. Stroke volume was determined using the product of left ventricular outflow tract area and time-velocity integral on pulsed-wave Doppler. Cardiac function was analyzed under basal conditions and in response to the β-AR agonist ISO (10 μg or ~0.5 mg/kg).

Infarct Size

Infarcts were identified 15 days after reperfusion by the absence of autofluorescence, identified using a DAPI filter set (FIG. 8)[16]. Infarct size was quantified by analyzing five 10-μm sections from each heart. Images were taken of the entire section using a Keyence bz-x800 microscope, and the LV and infarct areas were measured by outlining the respective regions using the freehand selection tool in ImageJ. Infarct size was then calculated as a percentage of LV area [(infarct area/LV area)×100]. Sections were obtained from the upper, middle, and lower regions of the infarct in each heart. All sections were analyzed independently by two blinded observers, and the results were averaged.

Sympathetic Outgrowth Assay.

Cultures of dissociated sympathetic neurons were prepared from superior cervical ganglia (SCG) of newborn rats as described[17]. Cells were pre-plated for 1 hour to remove non-neuronal cells, and then 5,000 neurons/well were plated onto a 96 well plate (TPP) coated with poly-L-lysine (PLL, 0.01%, Sigma-Aldrich) and either laminin (10 μg/mL, Trevigen) or laminin and CSPGs (1-2 μg/mL, Millipore; concentration was calibrated to inhibit outgrowth by 50% and differed between batches). Neurons were cultured in serum free C2 medium[18, 19] supplemented with 10 ng/mL NGF (BD Biosciences), 100 U/mL penicillin G, and 100 μg/mL streptomycin sulfate (Invitrogen). Neurons were treated with either vehicle (DMSO) or the compounds HJ-01 or HJ-02 at various concentrations as described in figure legends. Live cell imaging was carried out using an Incucyte Zoom microscope (Essen BioScience), with 20x phase images acquired every 2 hrs over a 30 hr period. Neurite length was measured using Cell Player Neurotrack software (Essen BioScience) and used to calculate the neurite growth rate.

Compartmentalized cultures: Micro-fluidic chambers were generated by adding SYLGARD 184 silicone elastomer (Dow Corning) into a pre-cast mold, and heating at 50-60° C. for 2 hours. Cleaned chambers were placed in 10 cm culture dishes (Corning) pre-coated with 0.01% PLL. The axonal compartment was then coated with 10 μg/mL collagen or collagen+1 μg/mL CSPGs. SCG were placed in reduced growth factor Matrigel (BD Bioscience) within the cell body compartment. C2 media supplemented with 10 ng/mL NGF was added to both compartments and cultures were maintained at 37° C. in a humidified 5% $CO_2$ incubator. After 24 hrs, or when axons were first visible in the axonal compartment, images were acquired (t=0) and vehicle (5% DMSO), HJ-01, HJ-02, or chondroitinase ABC were added to the axonal compartment. Additional images were obtained 3 hours later (t=3), and a growth rate was calculated based on the distance extended during that 3 hour period.

Western Blotting

Immunoblotting protein samples were prepared using 4x XT sample buffer and 20x XT reducing reagent (Biorad). Samples were boiled for 10 minutes at 95° C. before being spun down and added to protein gels. To separate proteins by SDS-PAGE, Criterion pre-cast 4-12% gradient Bis-tris gels were used and run for 2 hours at 120V. Proteins were transferred to PVDF membranes by semi-dry transfer at 25V for 45 minutes. Protein laden PVDF membranes were blocked for 1 hour in 5% milk dissolved in TBST. Membranes were briefly rinsed with TBST and incubated with primary antibodies diluted in 5% BSA TBST for either 1 hour at room temperature or overnight at 4° C. depending on the antibody. Following primary incubation blots were rinsed with TBST 3 times for 10 minutes each and placed in HRP-conjugated lgg secondary diluted in 5% milk TBST for 1 hour at room temperature. Blots were rinsed 3 times for 10 minutes each and imaged using SuperSignal HRP chemiluminescent substrate (ThermoFisher Scientific).

Immunohistochemistry

Tissue was collected 14 days after surgery, fixed in 4% paraformaldehyde, frozen and 10μm sections generated. Immunohistochemistry for tyrosine hydroxylase (TH; sympathetic nerves) and fibrinogen (Fib; infarct/scar) was carried out as described previously[11,20] {Lorentz, 2010 #7610} using rabbit anti-TH (1:1000, Millipore Sigma AB152) and Alexa Fluor 488-conjugated rabbit IgG-specific antibody (1:500, Molecular Probes), together with sheep anti-Fibrinogen (1:300; AbD Serotec 4440-8004) and Alexa Fluor —-conjugated sheep IgG-specific antibody (1:500, Molecular Probes). Sections were incubated with $NaBH_4$ and $CuSO_4$ in order to decrease autofluorescence. Slides were rinsed 3×10 minutes with PBS, coverslipped and visualized by fluorescence microscopy. Staining was quantified using the thresholding tool in ImageJ in a least 5 sections from each heart. TH+ fiber density was quantified within the infarct and the area immediately adjacent to the infarct (Peri-infarct).

For vascular analysis, formalin fixed paraffin embedded tissue was sectioned and four slides, each containing three 5μm sections, were processed from each heart. Sections were deparaffinized, stained with hematoxylin (S3301, Dako, Santa Clara, CA), and scanned at 20× magnification on an Aperio AT2 (Leica Biosystems, Wetzlar, Germany). After the hematoxylin stain, sections were subjected to sequential immunohistochemistry with 2 different antibodies using a method adapted from Tsujikawa and colleagues[23]. Antigen retrieval [boiling 15 minutes in a pH 6.0 Citra solution (BioGenex, Fremont, CA)], endogenous peroxidase blocking [20 minutes at room temperature in 0.6% $H_2O_2$ Dako Dual Endogenous Enzyme Block (S2003, Dako, Santa Clara, CA)], and protein blocking (10 minutes at room temperature with 5% normal goat serum and 2.5% BSA in TBST) were carried out before antibody addition. Primary antibody was added (a-SMA, 1:200, Abcam, ab5694; or CD31, 1:100, LSBio, 4737) for 60 minutes at room temperature and slides were washed 3×2 minutes in TBST. Anti-rabbit Histofine Simple Stain MAX PO horseradish peroxidase (HRP)- conjugated polymer (Nichirei Biosciences, Tokyo, Japan) was added for 30 minutes at room temperature, slides were again washed 3×2 minutes in TBST, and antibody was visualized using AEC chromogen (Vector Laboratories, Burlingame, CA). After visualization the process was repeated using the second antibody.

Image Processing and Cell Classification for Vascular IHC

Regions of interest were selected based on tissue quality after cyclic staining. Selection of regions were annotated in Aperio ImageScope (Leica Biosystems, Wetzlar, Germany) and saved as an XML file. Images from each slide were scanned with the same scan settings to generate images with identical dimensions for image registration. Registration was performed in MATLAB version 2018b (The MathWorks, Inc., Natick, MA) using the detectSURFfeatures algorithm from the Computer Vision Toolbox. Key points were identified from the final hematoxylin image and used as target points to register each AEC stained image from all cycles and rounds. The hematoxylin image was used to generate a nuclei segmentation mask using a custom macro in FIJI. The FIJI macro uses Color_Deconvolution [H AEC] to separate hematoxylin OD, followed by additional filtering steps for background subtraction and signal cleaning leading to a series of watershed and erosion-dilation steps used to generate the final binary mask. AEC signal was extracted using an RGB to CMYK conversion which utilizes a maximum gray component replacement to subtract the lowest brightness level from all channels. AEC chromogen signal is separated into the 'Y' channel and the middle 90% of pixels are rescaled to 0-255. Markers that were selected for marker-based segmentation were used to generate a secondary mask for each marker while maintaining the index of each cell from the labeled nuclei mask. Cytoplasmic segmentation boundaries were identified using a seeded watershed approach where the nuclei centroid served as the seed and the signal extracted marker provided boundaries for each cell. Signal extracted images were measured for mean intensity within the nuclei and cytoplasmic segmentation boundaries in Cell Profiler to obtain a matrix of single cell mean intensity measurements, area, and X,Y centroid positions for each cell. This matrix, along with the labeled masks, were imported into FCS Express Image Cytometry (De Novo Software, Glendale, CA) for single cell gating. The gating strategy was designed to evaluate endothelial and smooth muscle cells, where endothelial cells were defined as CD31+, and smooth muscle cells were defined as α-smooth muscle actin (α-SMA)+. Thresholds for each marker were manually set and visually validated within the hierarchical gating strategy by sampling random regions to determine optimal thresholds. Optimal thresholds were determined interactively by selecting cells from the gating scatter plot mean intensity signal and dynamically overlaying the binary mask on extracted signal until the mask appropriately selects positive cells. All subsequent image regions utilized the set threshold and were run in a batch based on the gating template in order to identify the total endothelial and smooth muscle cells in the analyzed region. The results are cell counts for gate defined cell types per region.

Cell Signaling

TrkB-HEK-293t cells (a kind gift from Dr. Moses Chao, NYU) were used to examine the effects of HJ01 and HJ02 on TrkB stimulated ERK phosphorylation. Cells were plated on 6-well plates in HG-DMEM (Gibco) with 10% FBS (Hyclone), 1% Penicillin/streptomycin (Gibco) and Geniticin (400 μg/mL; Life Technologies). At the appropriate density cells with rinsed twice with 1x PBS and media was replaced with Opti-MEM (Gibco) containing 2% FBS. Cells were transfected with Lipofectamine 2000 (7 μL per well) and with either 2.5 μg full-length PTPσ plasmid or 1 μg GFP control plasmid per well. After 6 hours cells were rinsed once with 1x PBS and replaced with regular growth media and grown for 12 hours. Cells were then serum starved for 2 hours in HG-DMEM+B27. Following serum starving cells were incubated with either HJ01 or HJ02 at 10 nM, 100 nM, or 1 uM for 1 hour and then stimulated with 5 ng/mL for 5 minutes. Cells were then rinsed with ice-cold PBS and lysed on ice with intermittent agitation for 30 minutes with Erk lysis buffer [50 mM Tris (pH 8.0), 150 mM NaCl, 2 mM EDTA, 10 mM NaF, 10% glycerol, and 1% NP-40] containing protease inhibitor cocktail (Roche), phosphatase inhibitor cocktails (Sigma), and 5 mM iodoacetamide. Lysates sat on ice for 30 min and were then treated with 10 mM dithiothreitol to inactive any remaining iodoacetamide. Protein lysate was cleared by centrifugation at 13,000×G for 10 minutes. The soluble fraction was removed and diluted with 4x XT sample buffer and 20x XT reducing reagent (Biorad) for western blot analysis as described above. Blots were probed with phospho-Erk (1:1000 Phospho-p44/42MAPK, Cell Signaling #9102) and Total-Erk (1:1000 p44/42MAPK, Cell Signaling #9101) antibodies.

The human hepatoma cells (HepG2; ATCC) were cultured in low glucose DMEM (Life Technologies) supplemented with 10% FBS (ATCC). HepG2 cells were serum starved for 1.5 hours, and were then treated with DMSO, 5 μM CinnGel 2ME (a PTP1B inhibitor; Santa Cruz), 1 μM HJ-01 or 1 μM HJ-02 for another 1.5 hours. Cells were then stimulated with 100 nM insulin for 5 min. Cells were washed and lysed as described above.

Immunoprecipitation Assay

To test the hypothesis that small molecules HJ-01 and HJ-02 disrupt the binding of TrkA and PTPσ, HEK-293t cells were transfected with a full length PTPσ plasmid and a TrkA-RFP plasmid (Addgene plasmid #24093) and pulled down using RFP-trap nanobody conjugated to magnetic agarose (Chromotek). HEK-293t cells were plated onto 6-well plates coated with 0.01% poly-1-lysine (Sigma) in high-glucose DMEM (Gibco) supplemented with 10% FBS (Hyclone) and 1% Anti-Anti (Gibco). 12 hours later cells were rinsed with lx PBS and media was replaced with Opti-MEM (Gibco) containing 2% FBS. Cells were transfected using Lipofectamine 3000 (Thermofisher Scientific). For transfection, 1 μg of TrkA-RFP and 1 μg of PTPσ plasmid, 6 μL of P3000 reagent, and 5 μL of lipofectamine reagent were added to each well of the 6-well plate. 12-16 hours later cells were rinsed twice with 1xPBS and media was replaced with DMEM and B27 supplement (Gibco) and serum starved for 4 hours. Following serum starving cells with treated small molecules or vehicle (DMSO) for 1 hour and then stimulated for an additional hour with 50 ng/mL Nerve growth factor (Alomone Labs #N-100) and 2 μg/mL Chondroitin Sulfate Proteoglycans (EMD-Millipore CC117). Cells were rinsed twice with ice-cold 1x PBS and lysed with IP lysis buffer (150 mM NaCl, 50 mM Hepes, 1.5 mM $MgCl_2$, 1 mM EGTA, 1% Triton-X, 10% glycerol, 1x Roche complete protease inhibitor cocktail, and 1x Sigma phosphatase inhibitor cocktails 2 and 3). Two wells of each 6-well plate were used for each condition and pooled after lysis for 30 minutes on ice with intermittent vortexing. Protein lysate was cleared by centrifugation at 13,000×G for 10 minutes leaving the soluble fraction. 10% of this lysate was set aside as the input fraction. TrkA immunoprecipitation was accomplished using 15 μL of RFP-trap magnetic agarose added to the remaining lysate and incubated overnight at 4° C. on a rotator. The protein bound to the RFP-trap agarose was then separated using a magnet and rinsed 3 times for 10 minutes each. To remove the protein from the beads, 4x XT-sample buffer (Biorad) was diluted to 2x using the IP lysis buffer and XT reducing reagent was added the sample was then incubated at 95° C. for 10 minutes and separated from the beads using a magnet. Samples were subjected to the standard western blotting protocol and probed for TrkA (1:1000; Millipore Sigma #06-574) and PTPσ (1:500; Proteintech #13008-1-AP). To quantify pulldown of PTPσ by TrkA-RFP the levels of each protein in the pulldown were quantified by pixel density, normalized to the respective input levels and then the ratio of PTPσ to TrkA was calculated and compared across samples.

PTPσ D1 D2 Protein Purification

D1D2 plasmid was a gift from (Brad Lang and Jerry Silver, Case Western Reserve University). Rosetta 2 (DE3) competent cells (Novagen) were transformed with 1 μL of D1D2 DNA and grown overnight at 37° C. on LB agar plates supplemented with kanamycin and chloramphenicol. A ¼ swath of the bacteria from the LB agar plate was spiked into 50 mL of LB media (with 50 μg/mL kanamycin and 34 μg/mL chloramphenicol) and grown at 37° C. overnight with 225 rpm shaking. The next day the 50 mL starter culture was pitched into 1 L of terrific broth (TB) media (12 g bacto tryptone, 24 g yeast extract, 0.4% glycerol, 17 mM KH2PO4, 72 mM K2HPO4, 1% glucose, 50 μg/ml Kanamycin, 34 μg/ml chloramphenicol) and grown at 37° C., 225 rpm until reaching an OD600 reading of 0.6. At this point the TB media was placed on ice and the protein expression of D1D2 was induced with 0.4 mM Isopropyl-β-thiogalactoside (IPTG, Sigma-Aldrich) and grown at 37° C. overnight, 225 rpm. Cells were harvested by centrifugation at 4000 rpm 4° C. for 15 min. The cell pellet was resuspended in 50mL of lysis buffer (20 mM HEPES, pH 7.5, 1 mM β-mercaptoethanol, 1 mM benzamidine, 0.2% NP-40, 0.2% Tween-20, 500 mM NaCl, 1 mM phenylmethylsulfonyl fluoride, 8.3 mg/L DNAse I) with a glass douncer and sonicated, on ice, 6 times for 30 seconds each time with 2 minutes rest between each cycle (Branson sonifier 450). The resulting lysate was cleared by centrifugation at 12,000×G, 4° C., for 30 minutes. Purification of the D1D2 protein was achieved using the attached his-tag by Ni-NTA affinity chromatography (Ni-NTA resin, Qiagen). The resulting purified protein was verified by size using 10% SDS-PAGE and subsequently by enzymatic activity assessment (see method below).

PTPσ D1 D2 Catalytic Activity Assessment

The catalytic activity of purified PTPσ D1D2 catalytic domain was assessed using p-nitrophenyl phosphate (pNPP, Sigma-Aldrich), a commonly used indicator of phosphatase activity. D1D2 is capable of using pNPP as a substrate and catalysis of the phosphate group results in a colorimetric reaction that can be monitored by 405 nm absorbance. The assay was conducted in ice cold 50 mM MES buffer with either 2 mM, 5 mM, or 10 mM pNPP. To this reaction mixture varying amounts of D1D2 protein were added (3 nM, 30 nM, or 300 nM) with either vehicle, 1 μM HJ-02, or 12.5 mM of sodium-orthovanadate (Sigma-Aldrich) as a control tyrosine phosphatase inhibitor. The reaction mixture was added to clear flat-bottom 96-well plates and kept on ice until the plate reading. A Spectra Max i3 (Molecular Devices) multi-well plate reader was used to measure 405 nm absorbance. The reaction was induced by incubation at 30° C. and measured continuously for 2 minutes.

Statistics

Student's t-test was used for comparisons of just two samples. Data with more than two groups were analyzed by one-way ANOVA using the Tukey post-hoc test to compare all conditions. For experiments comparing different surgical groups and a second variable (drug treatment) two-way ANOVA was carried out using the Bonferroni post-hoc test. All statistical analyses were carried out using Prism 8.

Results

Design and Synthesis of a PTPσ Inhibitor

We sought to identify an inhibitor of PTPσ, and were inspired by the natural product Illudalic acid which inhibits PTPσ and the related phosphatase LAR. Illudalic acid exhibits moderate potency ($IC_{50}$=~1 μM) against PTPα catalytic activity in vitro[24]. Illudalic acid contains an aldehyde as well as a hemi-acetal lactone that opens up to an aldehyde at physiological pH; the bis-aldehyde is required for activity, presumably because it is required to form a stable covalent bond with the active site cysteine of LAR/PTPσ. Because of (i) the cellular instability of the bis-aldehyde and (ii) the complex, multi-step synthesis of illudalic acid we envisaged a simpler analog with better physiochemical properties for in cell and in vivo studies. Inspired by illudalic acid and closely related analogs, we rationally designed two structurally related small molecules, HJ-01 and HJ-02. Similar to illudalic acid analogs, HJ-01 and HJ-02 are based on p-methoxy benzoic acid scaffold, however, the bis-aldehyde was replaced with an acrylamide group designed to react with the catalytic cysteine in PTPσ. HJ-01 and HJ-02 could be synthesized in four steps from commercially available starting material.

HJ-01 and HJ-02 Rescue Neurite Outgrowth Over CSPGs

CSPGs are potent inhibitors of central and peripheral neuron outgrowth. The primary CSPG receptor in sympathetic neurons is PTPσ, and removal of PTPσ allows sympathetic axons to grow over CSPGs[25,26]. To examine the efficacy of our small molecules, we asked if they could restore sympathetic axon outgrowth over inhibitory CSPGs. To test this, we performed live cell imaging of sympathetic neurons grown on plates coated with laminin or a combination of laminin and CSPGs. As expected, CSPGs significantly limited axon outgrowth (FIG. 1). Both HJ-01 and HJ-02 restored sympathetic axon outgrowth in a dose dependent manner (FIG. 1), with HJ-2 fully restoring growth at 30 nM and HJ-01 at 100 nM. In contrast, HJ-03, a structural analog of HJ-01 and HJ-02 in which the acrylamide was replaced with a non-reactive ethylamide isostere, did not promote sympathetic axon outgrowth across CSPGs (FIG. 1).

Figure 2A:
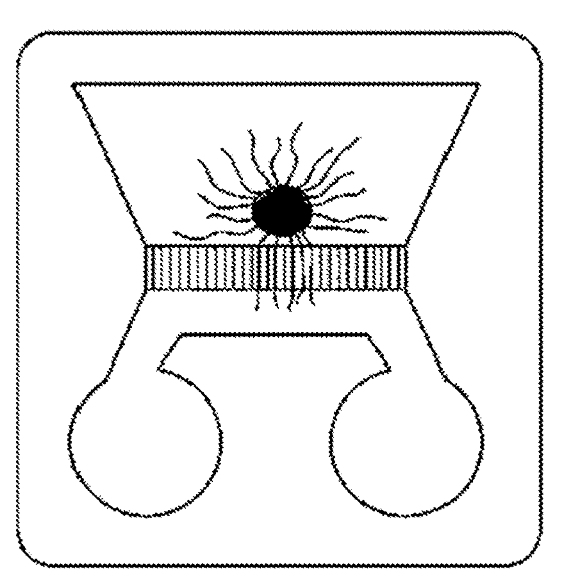
FIG. 2 provides (A) an illustration of microfluidic chambers, (B) representative images of axons in microfluidic chambers coated with CSPGs, and (C) quantification of axon growth rate in microfluidic chambers treated with HJ-01or HJ-02.
Figure 2B:
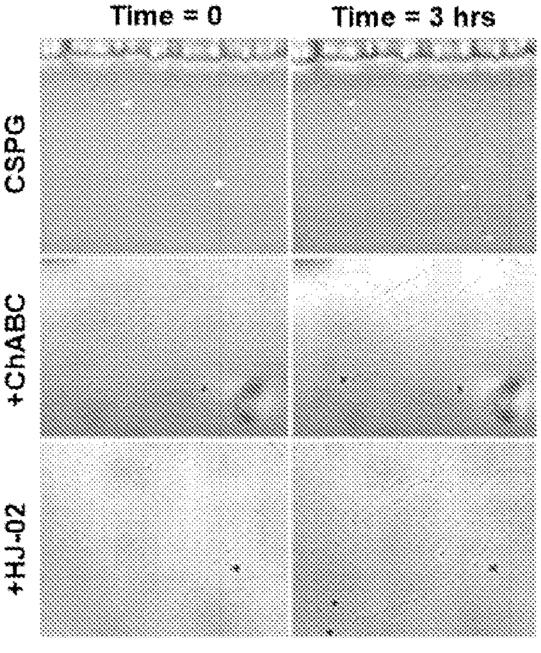
Figure 2C:
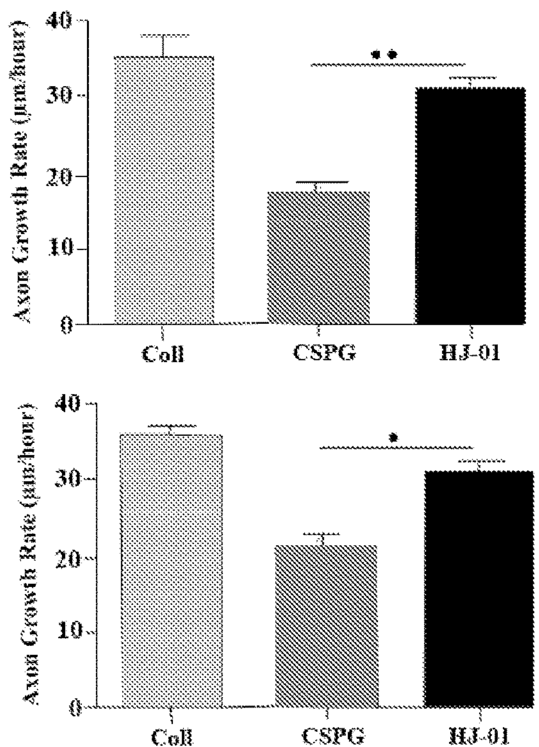

To confirm that the compounds acted on axons, sympathetic neurons were cultured in microfluidic chambers coated with either laminin or laminin+CSPGs in the distal compartment. After axons had extended into the distal compartment, media in that compartment was treated for 3 hours with vehicle, HJ-01, HJ-02, or chondroitinase ABC to disrupt CSPGs. Acute treatment with the small molecules or the positive control chondroitinase ABC stimulated the defasiculation of axon bundles growing over CSPGs and enhanced the rate of axon outgrowth (FIG. 2). The fast response to small molecule addition suggests they are acting within the axon to alter the rate of outgrowth.

HJ-01 and HJ-02 do not Inhibit Phosphatase Activity

Figure 3A:
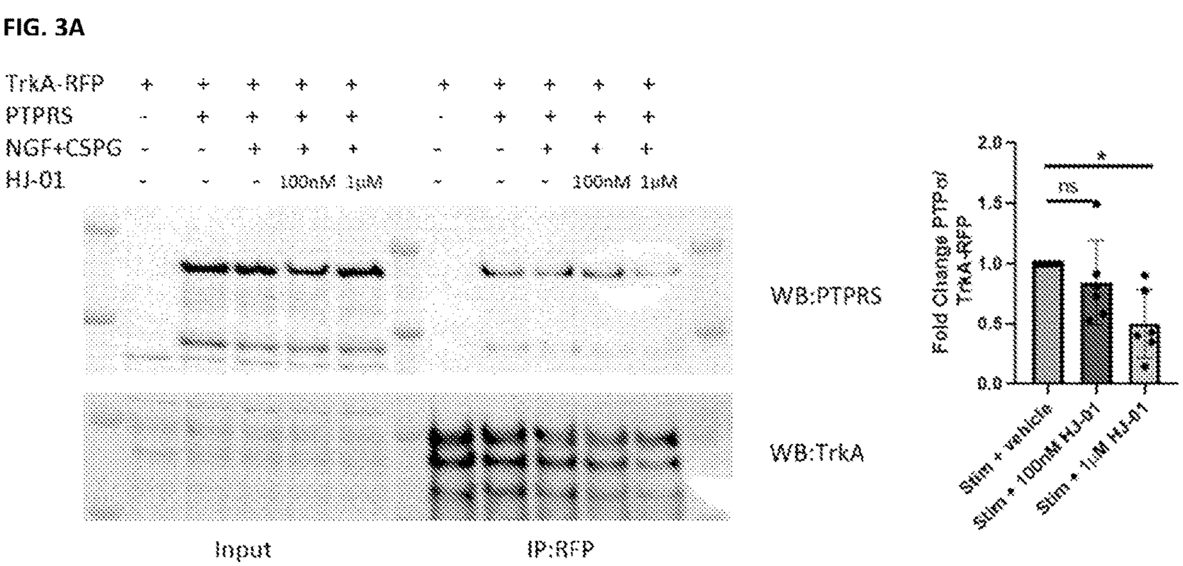
FIG. 3 provides representative western blots (left) probing for PTPRS and TrkA following TrkA-RFP immunoprecipitation. HEK-293 cells were transfected with TrkA-RFP and PTPRS, then treated with CSPGs, NGF, vehicle and either (A) HJ-01, (B) HJ-02, or (C) HJ-03.
Figure 3B:
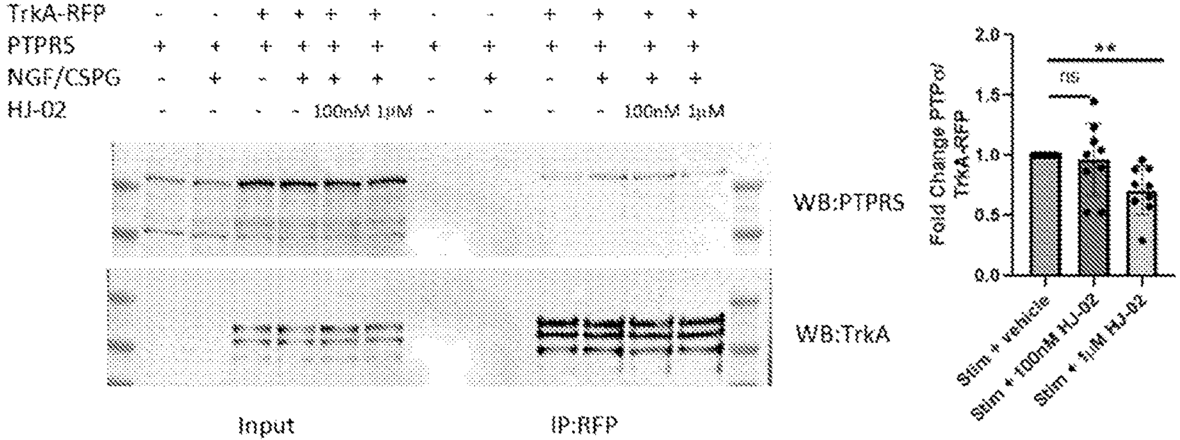
Figure 3C:
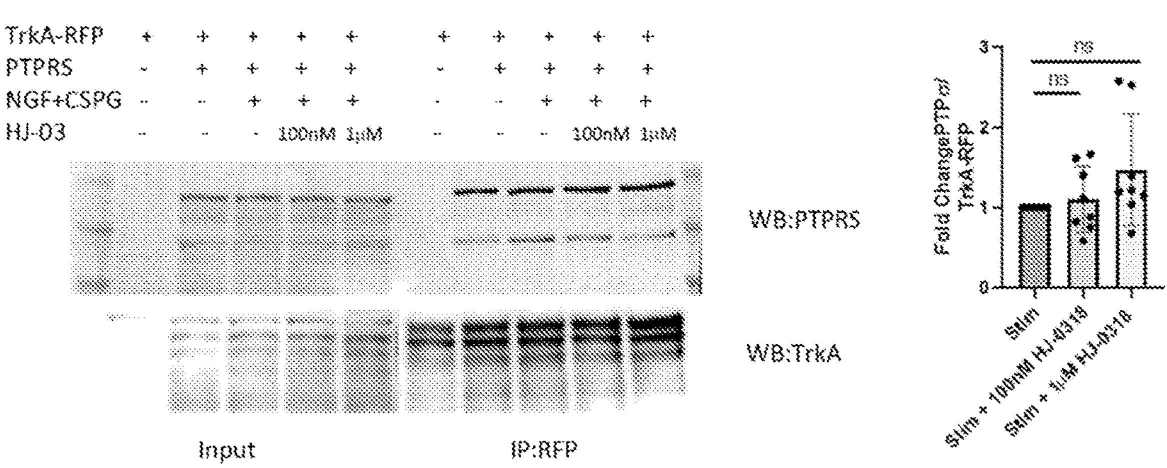

We hypothesized that HJ-01 and HJ-02 would irreversibly inhibit the catalytic activity of PTPσ by reacting with the active site cysteine in the D1 catalytic domain via a Michael addition. To test the hypothesis that these compounds inhibit PTPσ D1 catalytic activity, we expressed and purified a peptide including the D1 domain and the inactive D2 pseudocatalytic domain. We used the compound p-nitrophenolphosphate (pNPP) to monitor phosphatase activity through a colorimetric reaction. We incubated D1/D2 peptide with either vehicle (DMSO), 1 μM HJ-02, or the phosphatase inhibitor orthovanadate (10 mM) as a positive control. HJ-02 did not inhibit D1 phosphatase activity at 1 μM concentration, even though lower doses restored axon outgrowth in vitro. The samples treated with orthovanadate had negligible phosphatase activity as expected (FIG. 3). We also screened HJ-01 and HJ-02 against a panel of other protein phosphatases and found that neither HJ-01 nor HJ-02 inhibited any of the protein phosphatases in the screen (Supplement document X). These results show that HJ-01 and HJ-02 do not inhibit the catalytic activity of recombinant PTPσ as we had expected, and suggest that they impact PTPσ function via a different mechanism.

HJ-01 and HJ-02 Block TrkA—PTPσ Interactions

As is true for many enzymes, interaction of PTPσ with its protein substrates is required for efficient dephosphorylation. Trk tyrosine kinase receptors are critical substrates of PTPσ in neurons. Disrupting PTPσ or LAR binding to Trk receptors enhances Trk signaling[14] and axon outgrowth[12,13,27]. Thus, we asked if HJ-01 and HJ-02 altered the interaction between PTPσ and TrkA, the Trk receptor present in sympathetic neurons.

Figure 4A:
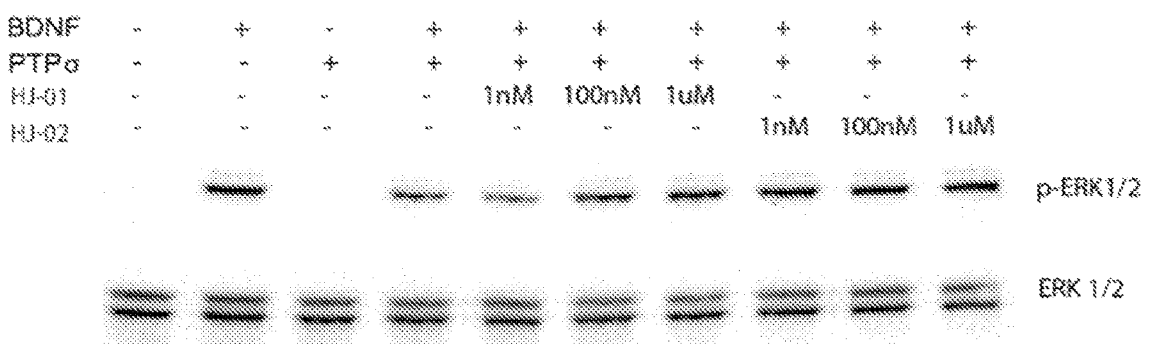
FIG. 4 provides representative Western blot looking at TrkB downstream signaling in the presence of PTPσ.
Figure 4B:
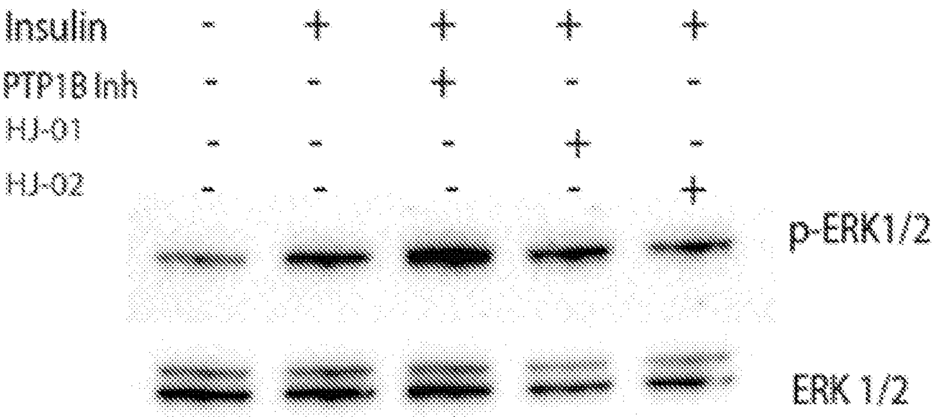
Figure 4C:
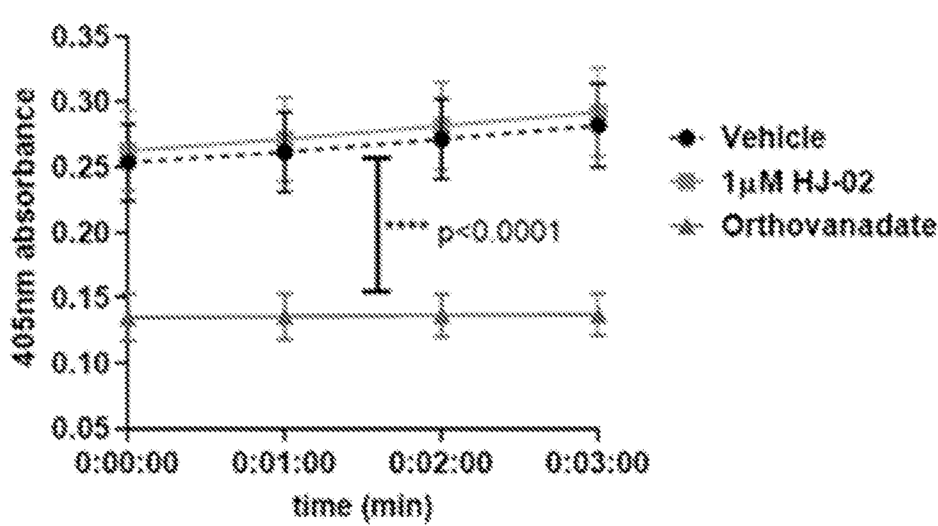

We transfected HEK 293T cells with PTPσ and TrkA tagged with red fluorescent protein (TrkA-RFP), and examined the ability of HJ-01 and HJ-02 to disrupt TrkA-PTPσ binding. Cells were treated simultaneously with NGF, CSPGs, and either vehicle (DMSO), HJ-01, HJ-02, or the biologically inactive compound HJ-03. These conditions were used to mimic the treatment conditions in sympathetic neurons. We immunoprecipitated TrkA-RFP using an RFP-nanobody conjugated to magnetic agarose, and compared the TrkA-PTPσ complex pulled down following HJ-01 or HJ-02 treatment with the amount pulled down in vehicle treated cells. The small molecules HJ-01 and HJ-02 disrupted the TrkA-PTPσ interactions as measured by pull-down efficiency, while the biologically inactive structural analog, HJ-03, did not disrupt TrkA—PTPσ binding (FIG. 4). This supports the model that HJ-01 and HJ-02 promote axon outgrowth by disrupting the interaction between PTPσ and TrkA.

HJ-01 and HJ-02 Reverse PTPσ-Inhibition of Trk Signaling

Figure 5:
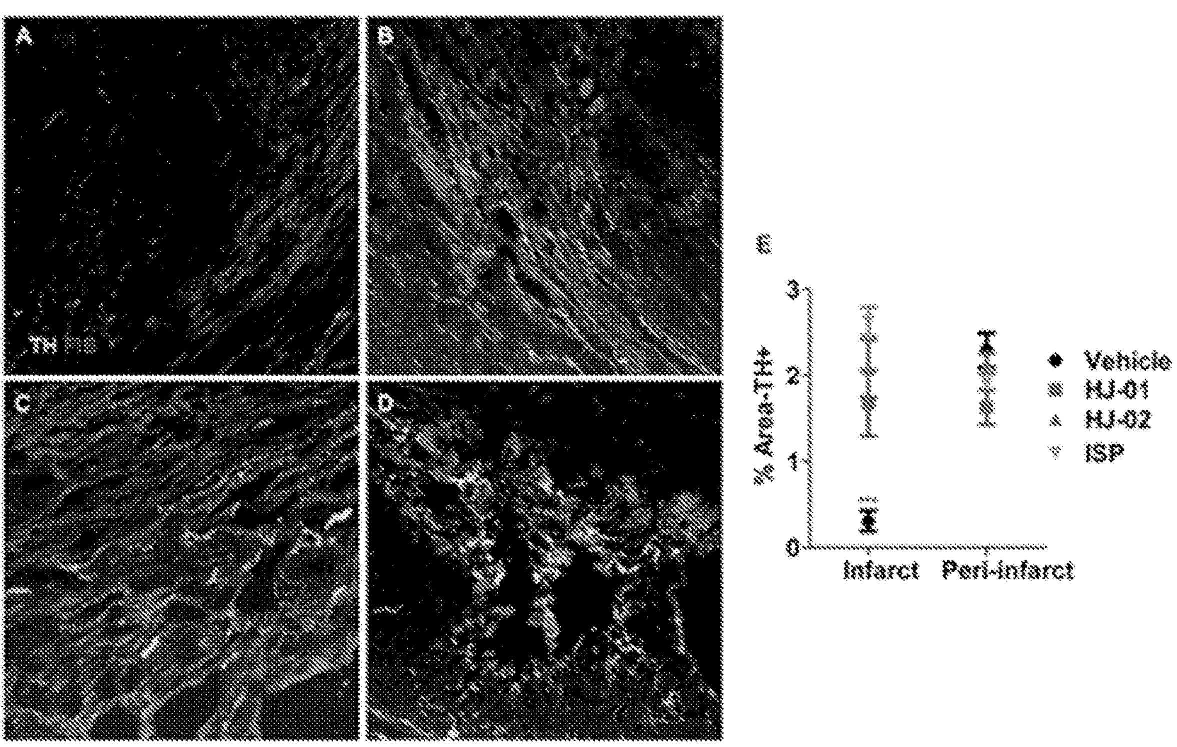
FIG. 5 provides representative images of infarcted LV from mice treated with (A) vehicle, (B) HJ-01, (C) HJ-02, and (D) ISP 14 days after MI, and (E) a quantification of TH+ fiber density within the infarct 14 days post-MI..

PTPσ dephosphorylates Trk receptors[15] and the absence of PTPσ enhances Trk signaling, noted by increased phosphorylation of downstream signaling proteins including ERK1/2 and Akt[28]. To determine disruption of Trk-PTP complexes by HJ-01 and HJ-02 prevented PTPσ inhibition of Trk signaling, we used HEK 293T cells stably expressing TrkB (HEK-TrkB). Co-expression of full-length PTPσ in HEK-TrkB cells decreased BDNF-induced ERK1/2 phosphorylation, and addition of HJ-01 or HJ-02 restored ERK1/2 phosphorylation to basal levels (FIG. 5). Similar to the neurite outgrowth data, HJ-02 was more potent than HJ-01, rescuing ERK1/2 phosphorylation at 10 nM rather than 100 nM.

As a negative control we asked if HJ-01 or HJ-02 disrupted signaling between tyrosine phosphatase PTP1B and its substrate the insulin receptor (IR-β)[29]. Both receptors are present in the human hepatic cell line HepG2. Insulin stimulation of IR-β in HepG2 cells increased phosphorylation of ERK1/2, and inhibiting PTP1B with CinnGel 2ME further enhanced ERK signaling. Conversely, HJ-01 and HJ-02 had no effect on ERK1/2 phosphorylation in insulin-stimulated HepG2 cells, indicating they do not inhibit PTP1B activity or otherwise disrupt PTP1B dephosphorylation of IR-β (FIG. 5). Taken together these results support the notion that HJ-01 and HJ-02 selectively inhibit PTPσ-mediated dephosphorylation of Trks by disrupting the interaction between PTPσ and Trks.

HJ-01 and HJ-02 Promote Sympathetic Reinnervation In Vivo

Figure 6A:
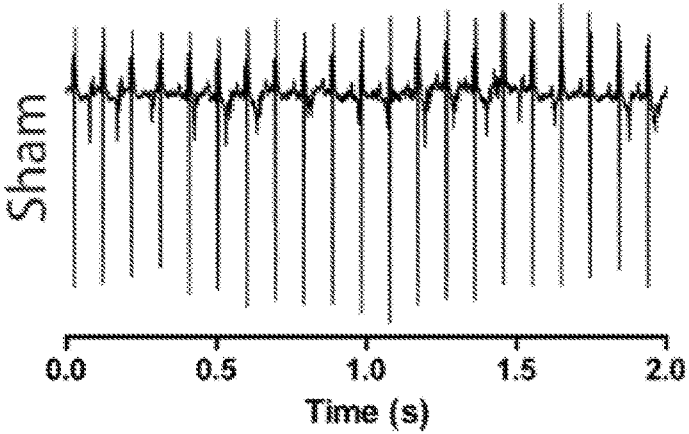
FIG. 6 provides representative electrocardiogram (ECG) traces recorded in conscious ambulatory animals following (A) sham or (B+C) MI then treated with either (B) vehicle or (C) HJ-02, and (D) quantification of arrythmias during the 45-minute period following isoproterenol injection in all groups.

We previously established that CSPGs within the infarct prevent reinnervation despite the presence of NGF[11], and that disruption of PTPσ restores sympathetic innervation to the infarct[11,13]. Since HJ-01 and HJ-02 promoted sympathetic axon outgrowth over CSPGs in vitro, we asked whether they could promote sympathetic nerve regeneration into the cardiac scar in vivo. Mice were treated on days 3-10 after surgery, and nerve density was quantified in the infarct and in viable tissue near the infarct (peri-infarct) on day 14. As expected, nerve density in sham animals was identical across all groups (FIG. 6). The infarcts in vehicle treated mice had significant nerve loss compared to sham animals and peri-infarct myocardium, while the infarcts in ISP, HJ-01, and HJ-02 treated mice did not. All three treatments restored nerve density within the infarct to the density in sham and uninjured peri-infarct myocardium (FIG. 6).

Reinnervation With HJ-01 and HJ-02 Prevents Arrhythmias

Figure 7D:
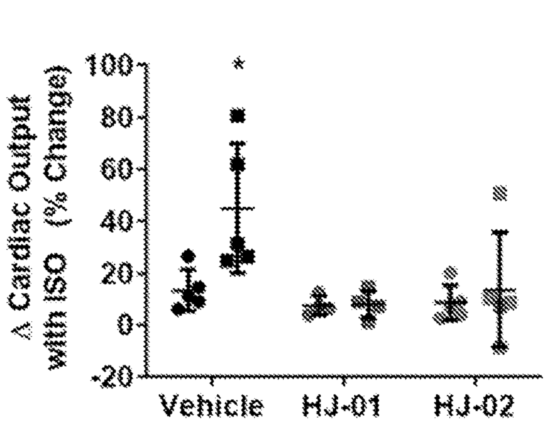
FIG. 7 provides graphs (A, B) representing quantification of cardiac output and ejection fraction in mice following sham or MI procedures, then treated with vehicle, HJ-01 or HJ-02, (C,D) quantification of the percent change in cardiac output and ejection fraction following injection of isoproterenol, (E) and an example image of a heart after MI depicting the loss of auto-fluorescence in the infarct, with the infarct outlined in white, and (F) quantification of infarct size as a percentage of left ventricle in mice treated with HJ-01, HJ-02, or ISP.
Figure 7E:
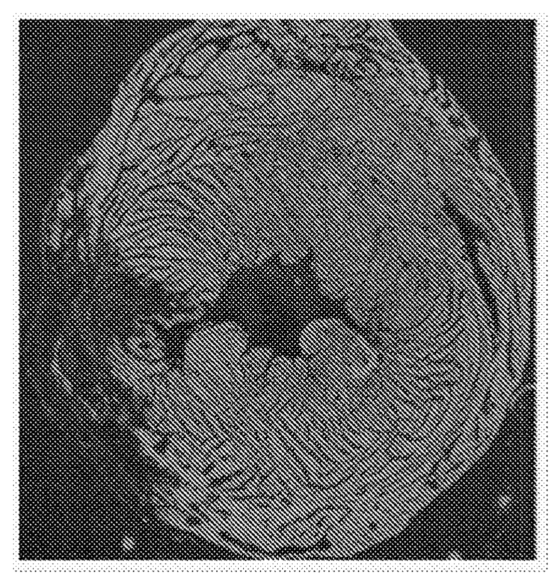
Figure 7F:
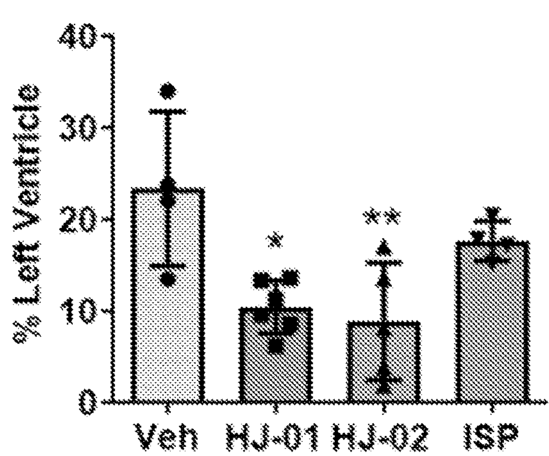
Figure 8A:
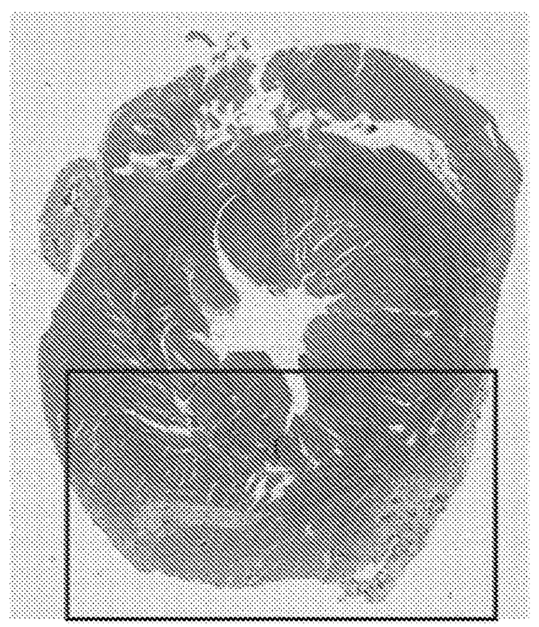
FIG. 8A depicts a vascular section micrograph labeled using antibodies to CD31.
Figure 8C:
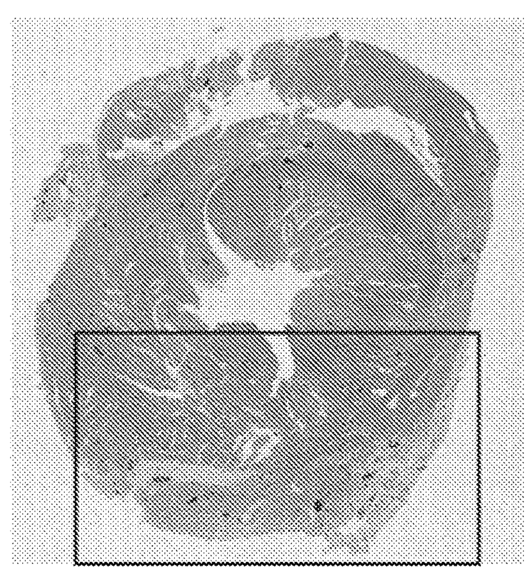
FIG. 8C depicts a vascular section micrograph labeled using antibodies to α-SMA.
Figure 8B:
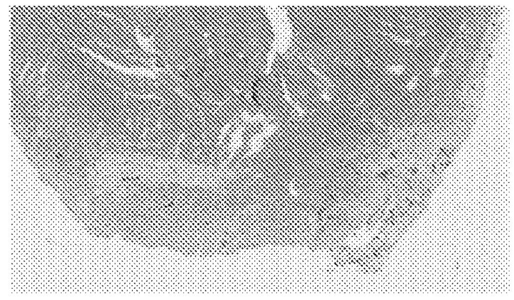
FIG. 8B provides and enlargement of the section indicated in 8A.
Figure 8D:
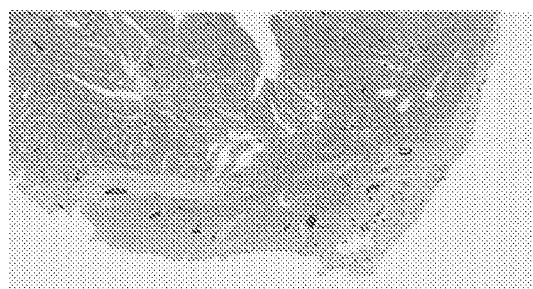
FIG. 8D provides and enlargement of the section indicated in 8C.
Figure 8E:
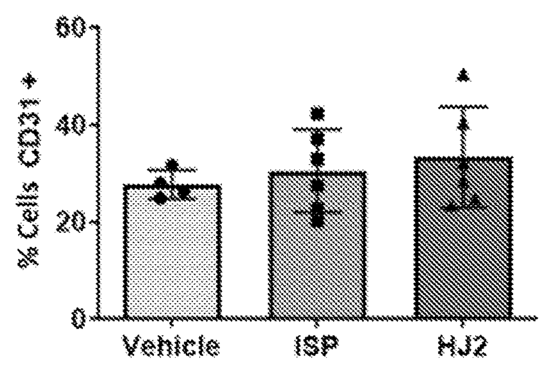
FIG. 8E provides bar graphs representing infarct differences in treated and untreated mouse hearts.

We previously showed that restoring innervation to the infarct with ISP treatment or PTPσ deletion made hearts less susceptible to arrhythmias[13]. To determine if restoring nerves using HJ-01 and HJ-02 prevented arrhythmias similarly, sham or MI mice with ECG telemetry implants were injected with 10 μg of the beta agonist isoproterenol (ISO) to mimic circulating catecholamines and provoke arrhythmias. ISO stimulated comparable increases in heart rate in all mice, and provoked few premature ventricular complexes (PVCs) in sham mice of all treatment groups. Post-MI mice treated with vehicle had significantly more ISO-stimulated PVCs than sham animals, while MI mice treated with ISP, HJ-01, or HJ-02 had arrhythmias similar to sham mice (FIG. 7).

HJ-01 and HJ-02 Prevent Loss of Cardiac Function and Reduce Infarct Size

Removal of PTPσ does not alter infarct size[13], but we do not know if treating mice with the novel small molecules HJ-01, or HJ-02 affects the health of cardiac myocytes, altering infarct size or cardiac output. To test that, we examined cardiac output and infarct size, using the HJ-01 and HJ-02 treated mice from the arrhythmia study (FIG. 7). Two independent observers, blinded to treatment group, analyzed each parameter. Cardiac output was measured by echocardiography 15 days after MI, which was 5 days after cessation of treatment and one day after the arrhythmia study. As expected, mice with an MI that were treated with vehicle had significantly reduced ejection fraction and cardiac output compared to sham mice (FIG. 8). Surprisingly, mice treated with HJ-01 or HJ-02 exhibited cardiac output and ejection fraction that was similar to sham animals treated with those compounds, and significantly higher than the MI animals treated with vehicle. Infarct size was then quantified using five 10 μm sections taken from the same hearts (FIG. 8). We found that treatment with HJ-01 or HJ-02 beginning three days after reperfusion led to significantly smaller infarcts compared to vehicle hearts. This unexpected outcome is consistent with the better cardiac output and ejection fraction in the HJ-treated hearts.

The protective effect of HJ-01 and HJ-02 on infarct size differed from our previous work in PTPσ-/-mice, which showed no change in infarct size[13]. We wondered whether this effect was specific to HJ-01 and HJ-02, or whether other pharmacologic interventions targeting PTPσ would have the same effect. We did not examine infarct size in our earlier ISP studies, as we expected that treating animals 3 days after reperfusion would not alter infarct size. Now we tested that assumption by treating mice with ISP on days 3-10 after MI, assessing cardiac function by echo on day 14, and then measuring infarct size. Interestingly, ISP had no effect on cardiac output or ejection fraction compared to vehicle treated animals, nor did it alter infarct size (FIG. 8). Thus, the effect of HJ-01 and HJ-02 in decreasing infarct size is likely due to a direct effect of the drugs rather than a result of reinnervation.

HJ-01 and HJ-02 Do Not Alter Cardiac Vascularization

A major contributor to extension of the infarct in the days following ischemia-reperfusion is microvascular damage[30], which is due at least in part to the loss of Trk signaling relative to p75 activation in vascular endothelial cells and pericytes[22]. Since HJ-01 and HJ-02 modulate Trk signaling, we hypothesized that HJ-01 and HJ-02 might be limiting infarct size by protecting the vasculature within the infarct and surrounding tissue. To quantify the vasculature 14 days after MI, we labeled sections using antibodies to α-smooth muscle actin (α-SMA, FIGS. 8C and 8D) and CD31 (FIGS. 8A and 8B), which identify vascular smooth muscle cells and endothelial cells, respectively. We found no difference in the density of vasculature between any treatment groups, regardless of location within the heart (FIG. 8). All MI treatment groups had similar vascular density in the infarct, viable peri-infarct tissue, and remote myocardium. Thus, HJ-01 and HJ-02 do not decrease infarct size by promoting revascularization. Additional studies will be required to identify the mechanisms by which these compounds protect the heart from damage after ischemia-reperfusion injury.

Discussion

There is a great need for therapeutics that can facilitate axon regeneration and cell migration through CSPG-laden scars. These compounds could promote axon outgrowth through inhibitory environments such as those present after spinal cord injury, traumatic brain injury, or myocardial infarction[12,13,27,31]. They might also enhance oligodendrocyte migration and differentiation to repair myelination in multiple sclerosis[32-34]. Using rational drug design, starting with the natural product illudalic acid as inspiration, we developed a series of small molecules covalently targeting the CPSG receptor PTPσ with an acrylamide group. Two of the compounds we generated, HJ-01 and HJ-02, restored axon growth through inhibitory CPSGs both in vitro and in vivo. A compound (HJ-03) lacking an acrylamide had no biological activity, suggesting that covalent binding was important for function. We found no evidence of widespread non-specific binding or toxicity, and the compounds were well tolerated in vivo. Importantly, there are several examples of FDA approved drugs (e.g. BTK inhibitor, Ibrutinib) that contain acrylamides, demonstrating that compounds with this type of electrophile are effective in vivo.

PTPσ regulation of axon dynamics depends on its ability to bind to and dephosphorylate substrate proteins including Trk tyrosine kinases[15]. Modulation of substrate binding can occur through two distinct mechanisms, one extracellular and one intracellular. Extracellular CSPGs bind to PTPσ monomers, which can then bind to and dephosphorylate substrate proteins like Trk receptors, decreasing axon outgrowth. In contrast, extracellular heparin sulfate proteoglycans (HSPGs) stimulate oligomerization of PTPσ into aggregates sequestered from Trk receptors, promoting axon outgrowth[35]. Intracellular binding of peptides or small molecules to the D2 pseudocatalytic domain of PTPσ can also disrupt substrate binding and enhance axon outgrowth[14]. We found that HJ-01 and HJ-02 did not block PTP phosphatase activity, but instead prevented PTPσ from interacting with Trk receptors, enhancing Trk signaling. This was most pronounced in the presence of CSPGs to stabilize PTPσ monomers. The disruption of the interaction between PTPσ-Trks by HJ-01 and HJ-02 in a cysteine-dependent manner is reminiscent of the disruption of IRAK4-MyD88 interactions by the multiple sclerosis drug dimethyl fumarate (DMF)[36].

Administration of HJ-01 and HJ-02 to mice several days after myocardial infarction restored sympathetic innervation to the CSPG-containing infarct. Restoring innervation with HJ-01 or HJ-02 prevented beta adrenergic receptor supersensitivity and isoproterenol-stimulated arrhythmias, consistent with earlier studies using ISP treatment and PTPσ deletion[13]. We expect that reinnervation stimulated by drug treatment prevents arrhythmias by normalizing cardiac electrophysiology and calcium handling in the same manner observed with PTPσ removal, but optical mapping studies will be required to confirm that hypothesis.

Although HJ-01, HJ-02, and ISP all restored innervation and decreased arrhythmia susceptibility, they had divergent effects on cardiac function and infarct size. We showed previously that systemic deletion of PTPσ had no effect on infarct size[13]. Human trials testing interventions to decrease infarct size often end 3 days after reperfusion[37], and we did not expect that any treatment begun 3 days after reperfusion in mice would alter infarct size or cardiac output. We measured those parameters in order to identify any potential toxicity of the novel compounds HJ-01 and HJ-02. When the study results were unblinded, we were surprised to discover that cardiac output in the HJ-treated MI mice was significantly higher than the vehicle- or ISP-treated MI mice and was similar to sham mice. The higher than expected cardiac output was explained by decreased infarct size in HJ-treated hearts compared to vehicle- or ISP-treated hearts. Quantification of echocardiography and infarct size were carried out by at least two independent observers who were blinded to the treatment groups, and all surgeries were carried out by a single person who was also blinded to subsequent treatment groups. Thus, the differences in cardiac function and infarct size seem to be due to divergent effects of ISP and the HJ compounds on extension of the cardiac scar several days after ischemia-reperfusion injury.

Neurotrophin signaling in the heart and vasculature is critical for proper development and for normal function in the adult [reviewed by Kermani, P. & Hempstead, B. BDNF Actions in the Cardiovascular System: Roles in Development, Adulthood and Response to Injury. *Frontiers in physiology* 10(2019)]. Neurotrophins and their receptors are increased in the heart after MI, and activation of TrkA and TrkB by neurotrophins or small molecules during cardiac ischemia can decrease infarct size[22,38-41]. In contrast, removing the p75 neurotrophin receptor (p75NTR), which also enhances Trk signaling[42], does not alter infarct size at 24 hours, [20] but prevents extension of the cardiac scar at 10 days after ischemia-reperfusion[22]. Since HJ-01 and HJ-02 enhance Trk signaling, we thought that they might prevent extension of the infarct by maintaining cardiac vascularization. However, we detected no difference in the cardiac vasculature of mice treated with HJ-01 or HJ-02 compared to mice treated with ISP or vehicle. This indicates that the beneficial effect of our compounds in the heart is through some other mechanism. Future studies will investigate the role of HJ-01 and HJ-02 in modifying cardiac inflammation and remodeling.

We generated novel small molecules targeting PTPσ in order to promote nerve regeneration through CSPG-containing scars. Two compounds that we generated restore nerve growth in vitro at nanomolar concentrations and restore nerve growth into the cardiac scar after myocardial infarction. These compounds had unexpectedly beneficial effects in the heart, increasing cardiac output and decreasing infarct size compared to vehicle. Although our focus was on the heart, CSPGs in the glial scar inhibit nerve regeneration after traumatic brain injury and spinal cord injury, preventing cognitive or motor recovery[31]. CSPG-PTPσ interactions also disrupt myelin repair in multiple sclerosis by inhibiting oligodendrocyte precursor cell (OPC) migration into demyelinated regions and preventing differentiation of OPCs into oligodendrocytes[32-34]. Our compounds or additional derivatives may prove useful to ameliorate disease progression in these situations. Small molecules are simpler to produce and easier to administer than the peptide (ISP) and enzyme (chondroitinase ABC)-based strategies that are the primary current focus of therapeutic development. Thus, these compounds provide an important advance in the development of therapies designed to overcome CSPG actions.

Figure Descriptions

FIG. 1. Compounds restore sympathetic neurite outgrowth over CSPGs in vitro. Quantification of sympathetic axon growth rate on Laminin or CSPGS in the presence of vehicle, HJ-01, HJ-02, HJ-03, or ISP. Data are mean±SEM 9 location/well and 3 wells per condition. *p<.05, **p<.01, and similar results were obtained in 3 separate experiments. X-Y plots on the left are representative individual experiments for each drug treatment, and bar graphs on the right are the summary of the 3 separate experiments.

FIG. 2. Axonal application of HJ-01 and HJ-02 is sufficient to promote sympathetic axon growth over CSPGs (A) Illustration of microfluidic chambers. (B) Representative images of axons in microfluidic chambers coated with CSPGs, taken at t=0 and t=3 hrs. Axons were treated with vehicle, ChABC, or compound HJ-02. Arrowheads identify the leading edge of the axon at t=0, and the asterisks identify the final position of the axon at t=3 hrs. (C) Quantification of axon growth rate in microfluidic chambers treated with HJ-01or HJ-02. Data are mean±SEM of at least 8 axons per condition. *p<.05, **p<.01, and similar results were obtained in 3 separate experiments.

FIG. 3. Compounds reduce the interaction between PTPRS and TrkA. Representative western blots (left) probing for PTPRS and TrkA following TrkA-RFP immunoprecipitation. HEK-293 cells were transfected with TrkA-RFP and PTPRS, then treated with CSPGs, NGF, vehicle and either (A) HJ-01, (B) HJ-02, or (C) HJ-03. Quantification (right) of PTPRS that co-immunoprecipitated with TrkA-RFP normalized to vehicle treated cells. HJ-01 and HJ-02 reduced the amount of PTPRS that bound to TrkA-RFP at 1 uM, but HJ-03 had no effect. Quantification is the summary of at least 5 experiments for each condition. Data are mean±SEM; *p<.05, **p<.01.

FIG. 4. HJ-01 and HJ-02 block PTPRS dependent reductions in TrkB signaling (A) Representative Western blot looking at TrkB downstream signaling in the presence of PTPσ. Both HJ-01 and HJ-02 restore p-ERK to normal levels in response to BDNF. (B) Western analysis examining potential off target effects of HJ-01 and HJ-02 on PTP1B activity in response to insulin. (C) Phosphatase activity assay of the catalytic D1D2 domain of PTPσ when treated with Vehicle, HJ-02, or the tyrosine phosphatase inhibitor orthovanadate.

FIG. 5. Subcutaneous HJ-01 and HJ-02 injections promotes sympathetic reinnervation of the infarct. (A-D) Representative images of infarcted LV from mice treated with (A) vehicle, (B) HJ-01, (C) HJ-02, and (D) ISP 14 days after MI. Sections were stained for TH to identify sympathetic nerve fibers and fibrinogen to identify the infarct. HJ-01, HJ-02, and ISP treatment resulted in extensive sympathetic reinnervation of the infarct. (D) Quantification of TH+ fiber density within the infarct 14 day post-MI (mean±SEM, n=5/group; ***p<.001).

FIG. 6. HJ compounds reduced arrhythmia susceptibility after MI. (A-C) Representative ECG traces recorded in conscious ambulatory animals following (A) sham or (B+C) MI then treated with either (B) vehicle or (C) HJ-02. Arrhythmias were induced by isoproterenol, and observed PVCs are noted with asterisks. (D) Quantification of arrhythmias during the 45 minute period following isoproterenol injection. Data are mean±SEM, n=5/group; ***p<.001.

FIG. 7. HJ-01 and HJ-02, but not ISP, reduce infarct size and preserve cardiac function. (A,B) Quantification of cardiac output and ejection fraction in mice following sham or MI procedures, then treated with vehicle, HJ-01 or HJ-02. (C, D) Quantification of the percent change in cardiac output and ejection fraction following injection of isoproterenol. (E) Example image of a heart after MI depicting the loss of auto-fluorescence in the infarct. (F) Quantification of infarct size as a percentage of left ventricle in mice treated with HJ-01, HJ-02 or ISP. Data are mean±SEM, n=5/group except sham n=4;*p<.05, p<.01, *p<.001.

1. Roth, G. A., et al. Global, Regional, and National Burden of Cardiovascular Diseases for 10 Causes, 1990 to 2015. *J Am Coll Cardiol* 70, 1-25 (2017).
2. Pfeffer, M. A. & Braunwald, E. Ventricular remodeling after myocardial infarction. Experimental observations and clinical implications. *Circulation* 81, 1161-1172 (1990).
3. Stanton, M.S., et al. Regional sympathetic denervation after myocardial infarction in humans detected noninvasively using I-123-metaiodobenzylguanidine. *J. Am. Coll. Cardiol.* 14, 1519-1526 (1989).
4. Barber, M. J., Mueller, T. M., Henry, D. P., Felten, S. Y. & Zipes, D. P. Transmural myocardial infarction in the dog produces sympathectomy in noninfarcted myocardium. *Circulation* 67, 787-796 (1983).
5. Inoue, H. & Zipes, D. P. Time course of denervation of efferent sympathetic and vagal nerves after occlusion of the coronary artery in the canine heart. *Circ. Res.* 62, 1111-1120 (1988).
6. Minardo, J. D., et al. Scintigraphic and electrophysiological evidence of canine myocardial sympathetic denervation and reinnervation produced by myocardial infarction or phenol application. *Circulation* 78, 1008-1019 (1988).
7 Li, W., Knowlton, D., Van Winkle, D. M. & Habecker, B. A. Infarction alters both the distribution and noradrenergic properties of cardiac sympathetic neurons. *Am. J Physiol Heart Circ. Physiol* 286, H2229-H2236 (2004).
8. Boogers, M. J., et al. Cardiac sympathetic denervation assessed with 123-iodine metaiodobenzylguanidine imaging predicts ventricular arrhythmias in implantable cardioverter-defibrillator patients. *J Am Coll Cardiol* 55, 2769-2777 (2010).
9. Nishisato, K., et al. Impaired cardiac sympathetic innervation and myocardial perfusion are related to lethal arrhythmia: quantification of cardiac tracers in patients with ICDs. *J Nucl Med* 51, 1241-1249 (2010).
10. Fallavollita, J. A., et al. Regional myocardial sympathetic denervation predicts the risk of sudden cardiac arrest in ischemic cardiomyopathy. *J Am Coll Cardiol* 63, 141-149 (2014).
11. Gardner, R. T. & Habecker, B. A. Infarct-derived chondroitin sulfate proteoglycans prevent sympathetic reinnervation after cardiac ischemia-reperfusion injury. *The Journal of neuroscience: the official journal of the Society for Neuroscience* 33, 7175-7183 (2013).
12. Lang, B. T., et al. Modulation of the proteoglycan receptor PTPsigma promotes recovery after spinal cord injury. *Nature* 518, 404-408 (2015).
13. Gardner, R. T., et al. Targeting protein tyrosine phosphatase sigma after myocardial infarction restores cardiac sympathetic innervation and prevents arrhythmias. *Nat Commun* 6, 6235 (2015).
14. Xie, Y., et al. Protein-tyrosine phosphatase (PTP) wedge domain peptides: a novel approach for inhibition of PTP function and augmentation of protein-tyrosine kinase function. *J Biol. Chem.* 281, 16482-16492 (2006).
15. Faux, C., et al. PTPsigma binds and dephosphorylates neurotrophin receptors and can suppress NGF-dependent neurite outgrowth from sensory neurons. *Biochim Biophys Acta* 1773, 1689-1700 (2007).
16. Parrish, D. C., et al. Transient denervation of viable myocardium after myocardial infarction does not alter arrhythmia susceptibility. *Am J Physiol Heart Circ Physiol*, ajpheart003002017 (2017).
17. Dziennis, S. & Habecker, B. A. Cytokine suppression of dopamine-beta-hydroxylase by extracellular signal-regulated kinase-dependent and -independent pathways. *J Biol Chem* 278, 15897-15904 (2003).
18. Lein, P., Johnson, M., Guo, X., Rueger, D. & Higgins, D. Osteogenic protein-1 induces dendritic growth in rat sympathetic neurons. *Neuron* 15, 597-605 (1995).
19. Pellegrino, M. J., Parrish, D. C., Zigmond, R. E. & Habecker, B. A. Cytokines inhibit norepinephrine transporter expression by decreasing Hand2. *Mol Cell Neurosci* 46, 671-680 (2011).
20. Lorentz, C. U., Woodward, W. R., Tharp, K. & Habecker, B. A. Altered norepinephrine content and ventricular function in p75NTR-/-mice after myocardial infarction. *Auton Neurosci* 164, 13-19 (2011).
21. Yang, X., et al. Discovery of novel inhibitor of human leukocyte common antigen-related phosphatase. *Biochim Biophys Acta* 1726, 34-41 (2005).
22. Gardner, R.T. & Habecker, B.A. Infarct-derived chondroitin sulfate proteoglycans prevent sympathetic reinnervation after cardiac ischemia-reperfusion injury. *J Neurosci.* 33, 7175-7183 (2013).
23. Shen, Y., et al. PTPsigma is a receptor for chondroitin sulfate proteoglycan, an inhibitor of neural regeneration. *Science* 326, 592-596 (2009).
24. Shen, Y., et al. PTPsigma is a receptor for chondroitin sulfate proteoglycan, an inhibitor of neural regeneration. *Science.* 326, 592-596 (2009).
25. Sapieha, P. S., et al. Receptor protein tyrosine phosphatase sigma inhibits axon regrowth in the adult injured CNS. *Molecular and Cellular Neuroscience* 28, 625-635 (2005).
26. Boutselis, I. G., Yu, X., Zhang, Z. Y. & Borch, R. F. Synthesis and cell-based activity of a potent and selective protein tyrosine phosphatase 1B inhibitor prodrug. *J Med Chem* 50, 856-864 (2007).

27. Bekkers, S. C. A. M., Yazdani, S. K., Virmani, R. & Waltenberger, J. Microvascular Obstruction: Underlying Pathophysiology and Clinical Diagnosis. *Journal of the American College of Cardiology* 55, 1649-1660 (2010).

28. Siao, C. J., et al. ProNGF, a cytokine induced after myocardial infarction in humans, targets pericytes to promote microvascular damage and activation. *J Exp Med* 209, 2291-2305 (2012).

29. Sherman, L. S. & Back, S. A. A 'GAG' reflex prevents repair of the damaged CNS. Trends *Neurosci.* 31, 44-52 (2008).

30. Ohtake, Y., Saito, A. & Li, S. Diverse functions of protein tyrosine phosphatase a in the nervous and immune systems. *Exp Neurol* 302, 196-204 (2018).

31. Luo, F., et al. Modulation of proteoglycan receptor PTPsigma enhances MMP-2 activity to promote recovery from multiple sclerosis. *Nat Commun* 9, 4126 (2018).

32. Pu, A., Stephenson, E. L. & Yong, V .W. The extracellular matrix: Focus on oligodendrocyte biology and targeting CSPGs for remyelination therapies. *Glia* 66, 1809-1825 (2018).

33. Coles, C. H., et al. Proteoglycan-Specific Molecular Switch for RPTPσ Clustering and
Neuronal Extension. *Science* 332, 484-488 (2011).

34. Zaro, B. W., et al. Dimethyl Fumarate Disrupts Human Innate Immune Signaling by Targeting the IRAK4-MyD88 Complex. *J Immunol* 202, 2737-2746 (2019).

35. Bulluck, H., Yellon, R. L. & Yellon, D. M. Promising strategies to minimize reperfusion injury in STEMI. *Minerva Cardioangiol* 64, 284-294 (2016).

36. Meloni, M., et al. Nerve growth factor promotes cardiac repair following myocardial infarction. *Circulation research* 106, 1275-1284 (2010).

37. Caporali, A., et al. Identification of the prosurvival activity of nerve growth factor on cardiac myocytes. *Cell death and differentiation* 15, 299-311 (2008).

38. Feng, N., et al. Constitutive BDNF/TrkB signaling is required for normal cardiac contraction and relaxation. *Proceedings of the National Academy of Sciences of the United States of America* 112, 1880-1885 (2015).

39. Fulgenzi, G., et al. BDNF modulates heart contraction force and long-term homeostasis through truncated TrkB.T1 receptor activation. *The Journal of cell biology* 210, 1003-1012 (2015).

40. Bothwell, M. Recent advances in understanding context-dependent mechanisms controlling neurotrophin signaling and function. *F*1000*Res* 8 (2019).

What is claimed:

1. A compound of Formula (II):

(II)

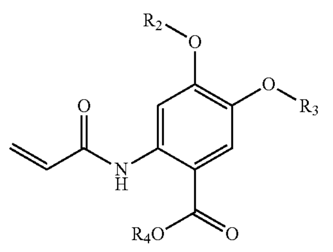

$R_2$ is selected from the group consisting of $C_1$-$C_4$ straight or branched alkyl, $C_2$-$C_4$ straight or branched alkenyl, and $C_2$-$C_4$ straight or branched alkynyl;

$R_3$ is selected from the group consisting of $C_2$-$C_8$ straight or branched alkyl, $C_2$-$C_6$ straight or branched alkenyl, and straight or branched $C_2$-$C_6$ alkynyl, $C_3$-$C_6$ cycloalkyl, and —$(CH_2)_{n1}$-$C_3$-$C_6$ cycloalkyl; and $R_4$ is selected from the group consisting of H, $C_1$-$C_6$ straight or branched alkyl, $C_2$-$C_6$ straight or branched alkenyl, $C_2$-$C_6$ straight or branched alkynyl, $C_3$-$C_6$ cycloalkyl, —$(CH_2)_{n2}$-$C_3$-$C_6$ cycloalkyl, $C_4$-$C_6$ cycloalkenyl, —$(CH_2)_{n2}$-$C_4$-$C_6$ cycloalkenyl, phenyl, —$(CH_2)_{n2}$-phenyl, 4-to 6-membered heterocyclyl, —$(CH_2)_{n2}$-4-to 6-membered heterocyclyl, heteroaromatic, and —$(CH_2)_{n2}$-heteroaromatic;

with the proviso that, when $R_4$ is hydrogen, then $R_3$ is not methyl;

or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

2. The compound of claim 1, wherein $R_2$ is selected from the group consisting of $C_1$-$C_4$ straight or branched alkyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

3. The compound of claim 1, wherein $R_2$ is selected from the group consisting of $C_1$-$C_3$ straight or branched alkyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

4. The compound of claim 1, wherein $R_2$ is selected from the group consisting of methyl and ethyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

5. The compound of claim 1, wherein $R_2$ is methyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

6. The compound of claim 1, wherein $R_3$ is selected from the group consisting of $C_2$-$C_6$ straight or branched alkyl, $C_2$-$C_6$ straight or branched alkenyl, and straight or branched $C_2$-$C_6$ alkynyl, $C_3$-$C_6$ cycloalkyl, and —$(CH_2)_{n1}$-$C_3$-$C_6$ cycloalkyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

7. The compound of claim 1, wherein $R_3$ is $C_2$-$C_6$ straight or branched alkyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

8. The compound of claim 1, wherein $R_3$ is selected from the group consisting of $C_2$-$C_6$ straight or branched alkenyl and straight or branched $C_2$-$C_6$ alkynyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

9. The compound of claim 1, wherein $R_3$ is selected from the group consisting of $C_3$-$C_6$ cycloalkyl and —$(CH_2)_{n1}$-$C_3$-$C_6$ cycloalkyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

10. The compound of claim 1, wherein $R_3$ is selected from the group consisting of cyclopropyl, cyclobutyl, cyclopentyl, cyclohexyl:

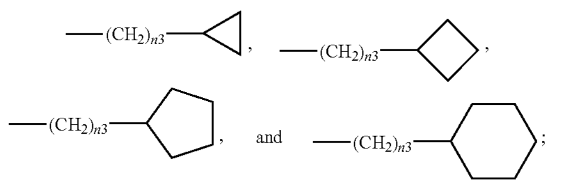

and n3 in each instance is an integer independently selected from the group consisting of 1, 2, 3, 4, 5, and 6;

or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

11. The compound of claim 1, wherein $R_3$ is selected from the group consisting of cyclopropyl and

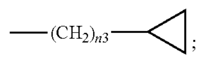

and n3 in each instance is an integer independently selected from the group consisting of 1, 2, 3, 4, 5, and 6;

or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

12. The compound of claim 1, wherein $R_3$ is selected from the group consisting of cyclobutyl and

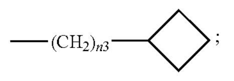

and n3 in each instance is an integer independently selected from the group consisting of 1, 2, 3, 4, 5, and 6;

or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

13. The compound of claim 1, wherein $R_3$ is selected from the group consisting of cyclopentyl and

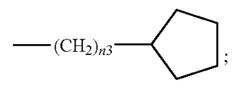

and n3 in each instance is an integer independently selected from the group consisting of 1, 2, 3, 4, 5, and 6;

or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

14. The compound of claim 1, wherein $R_3$ is selected from the group consisting of cyclohexyl and

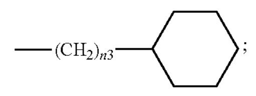

and n3 in each instance is an integer independently selected from the group consisting of 1, 2, 3, 4, 5, and 6;

or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

15. The compound of claim 1, wherein $R_4$ is selected from the group consisting of H, $C_1$-$C_6$ straight or branched alkyl, $C_3$-$C_6$ cycloalkyl, —$(CH_2)_{n2}$-$C_3$-$C_6$ cycloalkyl, phenyl, —$(CH_2)_{n2}$-phenyl, 4-to 6-membered heterocyclyl, —$(CH_2)_{n2}$-4-to 6-membered heterocyclyl, phenyl, and benzyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

16. The compound of claim 1, wherein $R_4$ is selected from the group consisting of H and $C_1$-$C_6$ straight or branched alkyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

17. The compound of claim 1, wherein $R_2$ is selected from the group consisting of methyl and ethyl; $R_3$ is $C_1$-$C_8$ straight or branched alkyl; and $R_4$ is selected from the group consisting of H and $C_1$-$C_6$ straight or branched alkyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

18. The compound of claim 1, wherein $R_2$ is selected from the group consisting of methyl and ethyl; $R_3$ is selected from the group consisting of cyclohexyl and

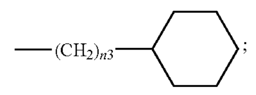

and $R_4$ is selected from the group consisting of H and $C_1$-$C_6$ straight or branched alkyl; or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

19. The compound of claim 1, selected from the group consisting of:

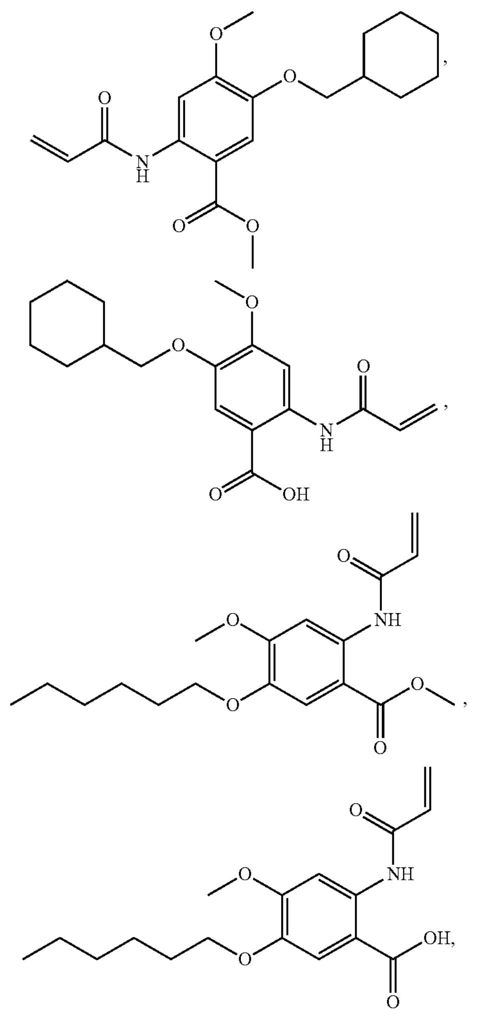

-continued

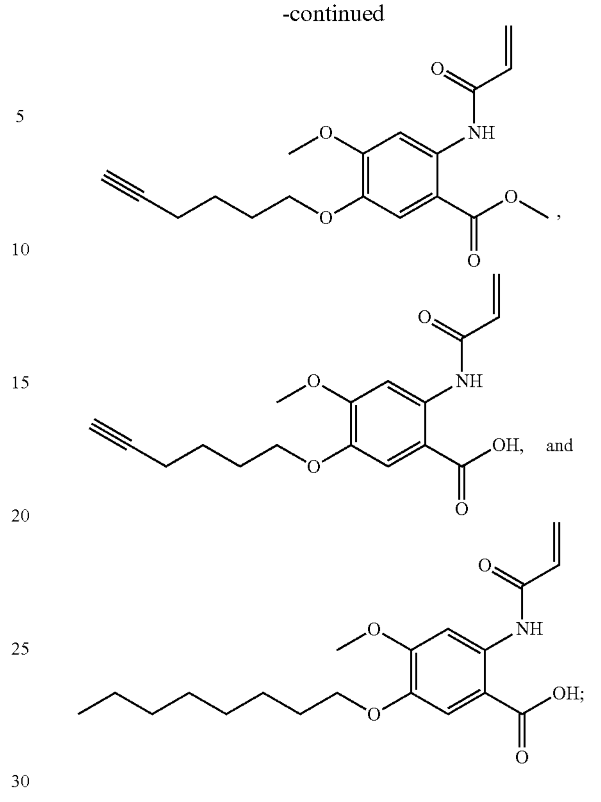

and or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

20. A pharmaceutical composition comprising a pharmaceutically acceptable carrier or excipient and a pharmaceutically effective amount of a compound of claim 1, or a pharmaceutically acceptable salt, pharmaceutically acceptable co-crystal, pharmaceutically acceptable ester, pharmaceutically acceptable solvate, hydrate, isomer, tautomer, isotope, polymorph, or a pharmaceutically acceptable prodrug thereof.

* * * * *